United States Patent
Credo et al.

(10) Patent No.: US 9,500,617 B2
(45) Date of Patent: Nov. 22, 2016

(54) NANOGAP TRANSDUCERS WITH SELECTIVE SURFACE IMMOBILIZATION SITES

(75) Inventors: Grace M. Credo, San Mateo, CA (US); Oguz H. Elibol, Palo Alto, CA (US)

(73) Assignee: Intel Corporation, Santa Clara, CA (US)

( * ) Notice: Subject to any disclaimer, the term of this patent is extended or adjusted under 35 U.S.C. 154(b) by 674 days.

(21) Appl. No.: 13/977,405

(22) PCT Filed: Dec. 28, 2011

(86) PCT No.: PCT/US2011/067520
§ 371 (c)(1), (2), (4) Date: Jun. 28, 2013

(87) PCT Pub. No.: WO2013/100949
PCT Pub. Date: Jul. 4, 2013

(65) Prior Publication Data
US 2014/0190824 A1    Jul. 10, 2014

(51) Int. Cl.
G01N 27/327 (2006.01)
G01N 27/30 (2006.01)
B82Y 15/00 (2011.01)
G01N 27/26 (2006.01)

(52) U.S. Cl.
CPC .......... G01N 27/308 (2013.01); B82Y 15/00 (2013.01); G01N 27/26 (2013.01); G01N 27/3277 (2013.01); G01N 27/3278 (2013.01)

(58) Field of Classification Search
CPC .................................... G01N 27/327–27/3277
See application file for complete search history.

(56) References Cited

U.S. PATENT DOCUMENTS

| | | |
|---|---|---|
| 5,849,487 A | 12/1998 | Hase et al. |
| 6,232,075 B1 | 5/2001 | Williams |
| 6,952,651 B2 | 10/2005 | Su |
| 7,005,264 B2 | 2/2006 | Su et al. |
| 7,208,077 B1 * | 4/2007 | Albers ............ G01N 27/3277  204/403.01 |
| 7,211,390 B2 | 5/2007 | Rothberg et al. |
| 7,488,578 B2 | 2/2009 | Gumbrecht et al. |
| 7,547,568 B2 | 6/2009 | Chou et al. |
| 7,575,865 B2 | 8/2009 | Leamon et al. |

(Continued)

FOREIGN PATENT DOCUMENTS

| | | |
|---|---|---|
| CN | 1828849 | 9/2006 |
| CN | 101389566 | 3/2009 |

(Continued)

OTHER PUBLICATIONS

JPO computer-generated English language translation of Arinaga et al. JP 2005-91246 A, patent published Apr. 7, 2005.*

(Continued)

Primary Examiner — Alexander Noguerola
(74) Attorney, Agent, or Firm — Trop, Pruner & Hu, P.C.

(57) ABSTRACT

Embodiments of the invention provide transducers capable of functioning as electronic sensors and redox cycling sensors. Transducers comprise two electrodes separated by a nanogap. Molecular binding regions proximate to and within the nanogap are provided. Methods of fabricating nanogap transducers and arrays of nanogap transducers are also provided. Arrays of individually addressable nanogap transducers can be disposed on integrated circuit chips and operably coupled to the integrated circuit chip.

34 Claims, 12 Drawing Sheets

(56) References Cited

U.S. PATENT DOCUMENTS

| | | | |
|---|---|---|---|
| 7,879,764 | B2 | 2/2011 | Su et al. |
| 7,923,240 | B2 | 4/2011 | Su |
| 8,262,900 | B2 | 9/2012 | Rothberg et al. |
| 8,372,585 | B2 | 2/2013 | Su et al. |
| 8,409,877 | B2 | 4/2013 | Liu et al. |
| 8,500,979 | B2 | 8/2013 | Elibol et al. |
| 8,524,057 | B2 | 9/2013 | Rothberg et al. |
| 8,563,240 | B2 | 10/2013 | Su et al. |
| 8,574,892 | B2 | 11/2013 | Su |
| 8,651,129 | B2 * | 2/2014 | Rapp ............... B01L 3/0293 137/208 |
| 2003/0152985 | A1 | 8/2003 | Hassibi et al. |
| 2003/0155942 | A1 | 8/2003 | Thewes |
| 2004/0005572 | A1 | 1/2004 | Rosner et al. |
| 2005/0012577 | A1 | 1/2005 | Pillans et al. |
| 2005/0019784 | A1 | 1/2005 | Su et al. |
| 2005/0019803 | A1 * | 1/2005 | Liu ................ B01J 19/0046 435/6.11 |
| 2005/0026163 | A1 | 2/2005 | Sundararajan et al. |
| 2005/0106587 | A1 | 5/2005 | Klapproth et al. |
| 2005/0214759 | A1 | 9/2005 | Wlassof et al. |
| 2006/0199193 | A1 | 9/2006 | Koo et al. |
| 2007/0117243 | A1 * | 5/2007 | Sharma ............. B81C 1/00063 438/49 |
| 2010/0084634 | A1 * | 4/2010 | Gamo ................ C23C 16/27 257/40 |
| 2010/0167938 | A1 | 7/2010 | Su et al. |
| 2010/0330553 | A1 | 12/2010 | Su et al. |
| 2011/0031983 | A1 | 2/2011 | David et al. |
| 2011/0155586 | A1 | 6/2011 | Elibol et al. |
| 2011/0159481 | A1 | 6/2011 | Liu et al. |
| 2011/0319276 | A1 | 12/2011 | Liu et al. |
| 2012/0046176 | A1 | 2/2012 | Credo et al. |

FOREIGN PATENT DOCUMENTS

| | | | |
|---|---|---|---|
| CN | 102203288 | | 9/2011 |
| JP | 2005-91246 | A * | 4/2005 ............ G01N 33/53 |
| WO | 03020946 | | 3/2003 |
| WO | 03/054225 | A2 | 7/2003 |
| WO | 2013/100949 | A1 | 7/2013 |

OTHER PUBLICATIONS

Show, et al., "Characterization and Electrochemical Responsiveness of Boron-Doped Nanocrystalline Diamond Thin-Film," Chemical Materials, American Chemical Society, Jan. 30, 2003, vol. 15, No. 4, pp. 879-888.

China Patent Office, Office Action mailed Apr. 15, 2015 in Chinese Patent Application No. 201180076004.2.

China Patent Office, Second Office Action mailed Oct. 19, 2015 in Chinese Patent Application No. 201180076004.2.

Japan Patent Office, Notice of Rejection mailed Jun. 2, 2015 in Japanese Patent Application No. 2014-548775.

International Preliminary Report on Patentability received for PCT Patent Application No. PCT/US2011/067520, mailed on Jul. 10, 2014, 5 pages.

International Search Report received for PCT Patent Application No. PCT/US2011/067520, mailed on Jul. 4, 2013, 3 pages.

Fritz et al., "Electronic detection of DNA by its intrinsic molecular charge," PNAS, Oct. 29, 2002, pp. 14142-14146, vol. 99, No. 22.

Zevenbergen et al., "Mesoscopic Concentration Fluctuations in a Fluidic Nanocavity Detected by Redox Cycling," Nano Letters, 2007, pp. 384-388, vol. 7, No. 2.

Elibol et al., "Localized heating and thermal characterization of high electrical resistivity silicon-on-insulator sensors using nematic liquid crystals," Applied Physics Letters, 2008, pp. 131908-1 to 131908-3, vol. 93, Issue 13.

Gabig-Ciminska et al., "Electric chips for rapid detection and quantification of nucleic acids," Biosensors and Bioelectronics, 2004, pp. 537-546, vol. 19.

Kling, "Ultrafast DNA sequencing," Nature Biotechnology, 2003, pp. 1425-1427, vol. 21, No. 12.

Ronaghi et al., "DNA Sequencing: A Sequencing Method Based on Real-Time Pyrophosphate," Science Magazine, 1998, pp. 363-365, vol. 281, No. 5375.

Yeung et al., "Electrochemical Real-Time Polymerase Chain Reaction," Journal of American Chemical Society, 2006, 4 pages, vol. 128, No. 41.

Wolfrum et al., "Nanofluidic Redox Cycling Amplification for the Selective Detection of Catechol," Analytical Chemistry, 2008, pp. 972-977, vol. 80, No. 4.

Rolka et al., "Integration of a Capacitive EIS Sensor into a FIA System for pH and Penicillin Determination," Sensors, 2004, pp. 84-94, vol. 4, No. 6.

Goluch et al., "Redox cycling in nanofluidic channels using interdigitated electrodes," Analytical and Bioanalytical Chemistry, 2009, pp. 447-456, vol. 394, No. 2.

Elibol et al., "Nanoscale thickness double-gated field effect silicon sensors for sensitive pH detection in fluid," Applied Physics Letters, 2008, pp. 193904-1 to 193904-3, vol. 92, No. 19.

Delucia et al., "An Error-prone family of Y DNA Polymerase (DinB homolog from Sulfolobus solfataricus) Uses a 'Steric Gate' Residue for Discrimination Against Ribonucleotides," Nucleic Acids Research, 2003, pp. 4129-4137, vol. 31, No. 14.

Gao et al., "Conferring RNA polymerase Activity to a DNA polymerase: A single residue in reverse transcriptase controls substrate selection," Proc. Natl. Acad. Sci. USA, Biochemistry, 1997, pp. 407-411, vol. 94.

Fuller et al., "The challenges of sequencing by synthesis," Nature Biotechnology, 2009, pp. 1013-1023, vol. 27, No. 11.

Eid et al., "Real-time DNA Sequencing from Single Polymerase Molecules," Science, 2009, pp. 133-138, vol. 323.

Rothberg et al., "An integrated semiconductor device enabling non-optical genome sequencing," Nature, 2011, pp. 348-352, vol. 475, No. 7356.

Wanunu et al., "Rapid electronic detection of probe-specific microRNAs using thin nanopore sensors," Nature Nanotechnology, 2010, pp. 807-814, vol. 5.

Ivanov et al., "DNA Tunneling Detector Embedded in a Nanopore," Nano Letters, 2010, pp. 279-285, vol. 11.

Margulies et al., "Genome sequencing in microfabricated high-density picoliter reactors," Nature, 2005, pp. 376-380, vol. 437.

Das et al., "Electrochemical Immunosensor Using p-Aminophenol Redox Cycling by Hydrazine Combined with a Low Background Current," Analytical Chemistry, 2007, pp. 2790-2796, vol. 79, No. 7.

Goldsmith et al., "Redox cycling and kinetic analysis of single molecules of solution-phase nitrite reductase," Proceedings of the National Academy of Sciences, 2011, pp. 17269-17274, vol. 108, No. 42.

Sun et al., "Electrochemistry of individual molecules in zeptoliter volumes," Journal of the American Chemical Society, 2008, pp. 8241-8250, vol. 130, No. 26.

Zevenbergen et al., "Stochastic Sensing of Single Molecules in a Nanofluidic Electrochemical Device," Nano Letters, 2011, pp. 2881-2886, vol. 11, No. 7.

Zevenbergen et al., "Fast Electron-Transfer Kinetics Probed in Nanofluidic Channels," Journal of the American Chemical Society, 2009, pp. 11471-11477, vol. 131, No. 32.

Oguz et al., "Nanoscale Thickness Double-gated Field Effect Silicon Sensors for Sensitive pH Detection in Fluid," Applied Physics Letters, 2008, pp. 193904 1-4, vol. 92.

Daniels et al., "Device and Method for Detecting Redox Reactions in Solution," U.S. Appl. No. 13/839,564, filed Mar. 13, 2013.

Katelhon et al., "Nanocavity Redox Cycling Sensors for the Detection of Dopamine Fluctuations in Micro Gradients," Anal. Chem., 2010, pp. 8502-8509, vol. 82.

Japan Patent Office, Notice of Reason for Rejection mailed Feb. 16, 2016 in Japanese Patent Application No. 2014-548775.

* cited by examiner

NANOGAP TRANSDUCERS WITH SELECTIVE SURFACE IMMOBILIZATION SITES

CROSS-REFERENCE TO RELATED APPLICATIONS

The present application is related to U.S. application Ser. No. 12/655,578 entitled "Nanogap Chemical and Biochemical Sensors," filed Dec. 31, 2009, now pending, U.S. patent application Ser. No. 11/226,696, entitled "Sensor Arrays and Nucleic Acid Sequencing Applications," filed Sep. 13, 2005, now pending, which is a continuation-in-part application that claims the benefit of U.S. patent application Ser. No. 11/073,160, entitled "Sensor Arrays and Nucleic Acid Sequencing Applications," filed Mar. 4, 2005, and U.S. patent application Ser. No. 11/967,600, entitled "Electronic Sensing for Nucleic Acid Sequencing," filed Dec. 31, 2007 now pending, the disclosures of which are incorporated herein by reference.

FIELD OF THE INVENTION

The embodiments of the invention relate generally to transducers, nanogap transducers, electronic sensing, electrochemistry, redox cycling, and biomolecule detection.

BACKGROUND INFORMATION

Analytic devices that provide increased accuracy and/or robustness, decreased need for analysis sample, and/or high throughput are valuable analytical and biomedical tools. Additionally, molecular detection platforms that are miniaturized and manufacturable in high volumes provide access to affordable disease detection to many people in places and situations in which such access was not in the past possible. The availability of affordable molecular diagnostic devices reduces the cost of and improves the quality of healthcare available. Additionally, portable molecular detection devices have applications in security and hazard detection and remediation fields and offer the ability to immediately respond appropriately to a perceived security or accidental biological or chemical hazard.

Genetic information in living organisms is contained in the form of very long nucleic acid molecules such as deoxyribonucleic acid (DNA) and ribonucleic acid (RNA). Naturally occuring DNA and RNA molecules are typically composed of repeating chemical building blocks called nucleotides. The human genome, for example, contains approximately three billion nucleotides of DNA sequence and an estimated 20,000 to 25,000 genes.

Determination of the entire three billion nucleotide sequence of the human genome has provided a foundation for identifying the genetic basis of many diseases, such as cancer, cystic fibrosis, and sickle cell anemia. Sequencing the genomes or sections of the genome of individuals provides an opportunity to personalize medical treatments. The need for nucleic acid sequence information also exists in research, environmental protection, food safety, biodefense, and clinical applications, such as for example, pathogen detection, i.e., the detection of the presence or absence of pathogens or their genetic varients.

DETAILED DESCRIPTION OF THE INVENTION

Figure 1:
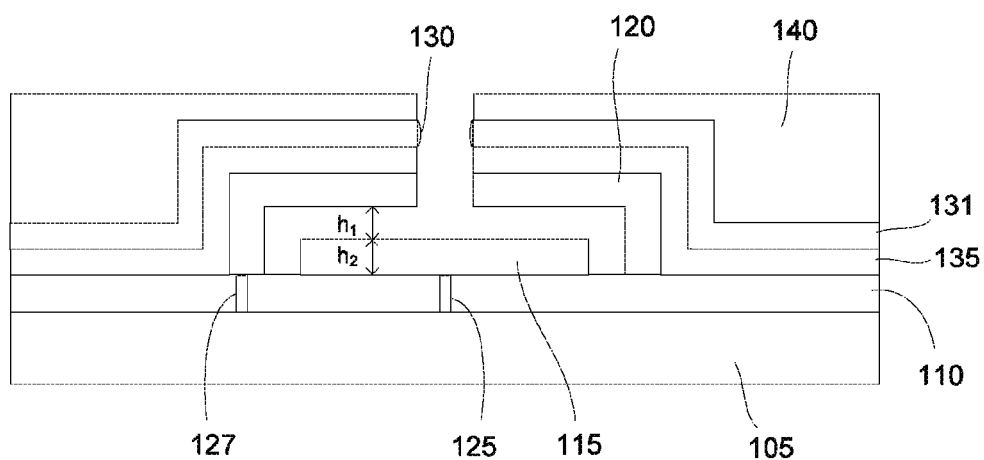
FIG. 1 is a schematic diagram illustrating a nanogap transducer.

The ability to detect biological reactions and molecules at ultra-low concentrations has applicability to, for example, molecular detection and analysis, molecular diagnostics, disease detection, substance identification, and DNA detection and sequencing. Embodiments of the invention provide electronic sensors that exhibit high sensitivity, extremely reduced footprints, and a high degree of manufacturability.

Nanogap transducers according to embodiments of the invention can be large arrays of sensors. For example, arrays of nanogap transducers can comprise 1000 to 10 million or one million to 10 billion transducers in which 50% or more, 75% or more, 85% or more, 90% or more, 95% or more, or 98% or more of the transducers are functioning sensors are provided.

Embodiments of the invention provide transducers capable of functioning as electronic sensors and redox cycling sensors. In general, redox cycling is an electrochemical method in which a molecule that can be reversibly oxidized and/or reduced (i.e., a redox active molecule) moves between at least two electrodes that are biased independently, one below a reduction potential and the other one above an oxidation potential for the redox active molecule being detected, shuttling electrons between the independently biased electrodes (i.e., the molecule is oxidized at a first electrode and then diffuses to a second electrode where it is reduced or vice versa, it is first reduced and then oxidized, depending on the molecule and the potentials at which the electrodes are biased). In redox cycling the same molecule can therefore contribute a plurality of electrons to the recorded current resulting in the net amplification of the signal.

In the nanogap transducers of embodiments of the invention, signal from chemical reactions being analyzed can be captured for a significant period of time near the sensor electrodes. Signal leakage away from the sensor region can be attenuated by closing the nanogap sensor during operation, such as, for example, with a bead that is located across the opening. Unlike other electronic detection techniques, it was found that the biomolecules being detected in embodiments of the invention do not have to be attached directly to the sensor electrodes. In embodiments of the invention, biomolecules to be detected can be attached proximate to the electrodes within the device interior.

Nanogap transducers according to embodiments of the invention can be reliably fabricated in a CMOS (complementary metal oxide semiconductor) compatible manner allowing dense integration of sensor units (and optionally driving electronics) onto a single platform, such as for example a chip or silicon wafer typically used in integrated circuit manufacturing applications. Because the nanogap transducers provided by embodiments of the invention are very small and very sensitive, they provide the ability to detect molecules and biomolecules at ultra-low concentrations in a massively parallel manner. An individual nanogap transducer can, for example, occupy as little as 0.5 µm² on an array or other chip surface. In other embodiments an individual nanogap transducer occupies between to as 0.5 µm² to 50 µm² or 0.5 µm² to 1.00 µm² of area on an array or other chip surface. The ability to detect molecules in a highly sensitive manner has applications in fields of diagnostics, proteomics, genomics, security and chemical and biological hazard detection.

FIG. 1 illustrates a nanogap transducer that is capable of functioning as an electronic sensor, detecting redox molecules, and/or functioning as a redox cycling sensor. In FIG. 1, a substrate 105 has a dielectric layer 110 and first electrode 115. A second electrode 120 is separated from the first electrode by a gap that has a height, $h_1$. In embodiments of the invention, the height of the gap, $h_1$, is less than 500 nm or between 10 and 200 nm, between 10 and 150 nm, or between 25 and 150 nm. Optional electronic interconnections 125 and 127, such as vias through dielectric layer 110, make connections to optional electronics (not shown) housed in the substrate 105. In embodiments of the invention, the substrate 105 is an integrated circuit (IC) chip and comprises electronics for, for example, driving electrodes 115 and 120, signal reading, signal amplification, and/or data output. The substrate can be other materials, such as, for example, glass, passivated metal, polymer, semiconductor, PDMS (polydimethylsiloxane), and/or flexible elastomeric substances. In embodiments in which the substrate does not house electronics, electrical connections to electrodes 115 and 120 can extend out along a surface of insulating layer 110 or through substrate 105, although other configurations are also possible.

The nanogap transducer of FIG. 1 comprises a molecular binding region 130 that is proximate to the electrodes 115 and 120. The molecular binding region 130 is comprised of a layer of preferentially functionalizable material 131. The molecular binding region 130 comprises the exposed region of the preferentially functionalizable material 131. The layer of preferentially functionalizable material 131 is between a first layer of dielectric material 135 and a second layer of dielectric material 140. The first layer of dielectric material 135 is an optional layer, and in embodiments of the invention the layer of preferentially functionalizable material 131 is disposed on the second electrode 120. The presence or absence of the first layer of dielectric material 135 in the device of FIG. 1 can depend on factors, such as the adhesion between the material that the second electrode is comprised of and the material that the preferentially functionalizable material 131 is comprised of. The layer of preferentially functionalizable material 131 is a material that can bind or attach linker molecules and/or biomolecules of interest preferentially as compared to the ability of the materials that comprise the exposed regions of the nanogap transducer (surface regions that under operational conditions come into contact with liquids) to bind or attach linker molecules or biomolecules of interest. In embodiments of the invention, the layer of preferentially functionalizable material 131 is comprised of silicon dioxide, and the first and the second layers of dielectric material 135 and 140 are comprised of silicon oxynitride. The exposed silicon dioxide region (molecular binding region 130) can be preferentially functionalized using a silane, such as, for example, aminopropyltriethoxysilane, when the electrodes 115 and 120 are comprised of platinum, palladium, gold, carbon materials (for example, diamond, graphitic carbon, or amorphous carbon), nickel, and/or indium tin oxide. In additional embodiments of the invention, the layer of preferentially functionalizable material 131 is comprised of hafnium oxide, aluminum oxide, or tantalum oxide and can be preferentially functionalized using a silane, such as, for example, aminopropyltriethoxysilane, when the electrodes 115 and 120 are comprised of platinum, palladium, gold, carbon materials (for example, diamond, graphitic carbon, or amorphous carbon), nickel, and/or indium tin oxide. In additional embodiments of the invention, the preferentially functionalizable layer 131 is comprised gold, platinum, or palladium, and the resulting molecular binding region 130 can be preferentially functionalized with molecules comprising a thiol (—SH) or disulfide (—S—S—) group, when the electrodes 115 and 120 are comprised of carbon materials, such as diamond, graphitic carbon, or amorphous carbon. Other materials for the preferentially functionalizable material 131 and dielectric layers 135 and 140 are also possible.

In embodiments of the invention, the molecular binding region 130 comprises a linker molecule, a combination of linker molecules, and/or a probe molecule. Linker molecules can be attached to the surface of the molecular binding region 130 and comprise a functional group that is capable of attaching to a molecule of interest (for example, a probe molecule or an additional linker molecule). Linker molecules can be chosen to selectively react with the molecular binding region 130 (but not with dielectric materials 135 and 140 or the electrode materials 115 and 120), and include molecules such as, for example, silanes, thiols, disulfides, isothiocynates, alkenes, and alkynes. Probe molecules are molecules that can selectively bind a target molecule of interest, such as, for example, sequences of DNA, sequences of RNA, biotin or avidin, and antibodies, antigens, receptors and their specific binding partners, proteins and their specific small molecule binding partners, and/or peptides. Probe molecules comprise one or more molecular recognition sites. Antibodies include, for example, polyclonal and monoclonal antibodies, as well as antigen binding fragments of such antibodies. An antibody or an antigen binding fragment of an antibody is characterized, for example, by having specific binding activity for an epitope of an analyte. The probe can be either member of a specific binding pair, such as, for example, immunological pairs such as antigen-antibody, biotin-avidin, hormones-hormone receptors, nucleic acid duplexes, IgG-protein A, and polynucleotide pairs such as DNA-DNA, and DNA-RNA. Probe molecules can be coupled to linker molecules through known coupling chemistries.

The electrodes 115 and 120 are comprised of a conducting material. In embodiments of the invention, the electrodes 115 and 120 are comprised of diamond, platinum, and/or gold. In additional embodiments of the invention, the electrodes 115 and 120 are comprised of palladium, nickel, graphitic carbon, amorphous carbon, and/or indium tin oxide. In embodiments of the invention, at least one electrode 115 or 120 is comprised of a conducting diamond material. In embodiments of the invention, electrode 115 is comprised of conducting diamond. In further embodiments of the invention, both electrodes 115 and 120 are comprised of conducting diamond material. Diamond can be made to conduct electricity by doping it, for example. Dopants include, for example, boron, nitrogen, and phosphorous. In an embodiment of the invention, the dopant is boron. Doping concentrations for boron doped diamond materials include concentrations greater than $10^{20}$ atoms/cm$^3$ and less than $10^{22}$ atoms/cm$^3$. In embodiments of the invention, when the first electrode 115 is comprised of a conducting diamond material, the height of the electrode, $h_2$, is between 200 and 1000 nm. In alternate embodiments, the height of the conducting diamond electrode, $h_2$, is between 5 and 25 nm. In embodiments of the invention, the conducting diamond film is microcrystalline or nanocrystalline diamond. In operation, typically a reference electrode (not shown) is also used with the nanogap transducer. The reference electrode is in contact with the solution which is being measured but does not have to be located within the nanogap.

Figure 2:
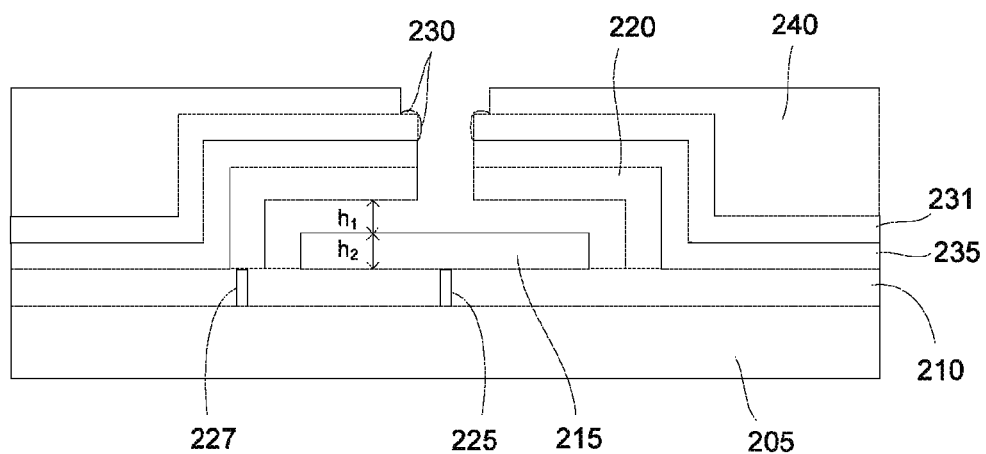
FIG. 2 is a schematic diagram illustrating an additional embodiment of a nanogap transducer.

FIG. 2 illustrates a nanogap transducer that is capable of functioning as an electronic sensor, detecting redox molecules, and/or functioning as a redox cycling sensor. In FIG. 2, a substrate 205 has a dielectric layer 210 and first electrode 215. A second electrode 220 is separated from the first electrode by a gap that has a height, $h_1$. In embodiments of the invention, the height of the gap, $h_1$, is less than 500 nm or between 10 and 200 nm, between 10 and 150 nm, or between 25 and 150 nm. Optional electronic interconnections 225 and 227, such as vias through dielectric layer 210, make connections to optional electronics (not shown) housed in the substrate 205. In embodiments of the invention, the substrate 205 is an integrated circuit (IC) chip and comprises electronics for, for example, driving electrodes 215 and 220, signal reading, signal amplification, and/or data output. The substrate can be other materials, such as, for example, glass, passivated metal, polymer, semiconductor, PDMS (polydimethylsiloxane), and/or flexible elastomeric substances. In embodiments in which the substrate does not house electronics, electrical connections to electrodes 215 and 220 can extend out along a surface of insulating layer 210 or through substrate 205, although other configurations are also possible.

The nanogap transducer of FIG. 2 comprises a molecular binding region 230 that is proximate to the electrodes 215 and 220. The molecular binding region 230 is comprised of a layer of preferentially functionalizable material 231. The molecular binding region 230 comprises the exposed region of the preferentially functionalizable material 231. The layer of preferentially functionalizable material 231 is between a first layer of dielectric material 235 and a second layer of dielectric material 240. The first layer of dielectric material 235 is an optional layer, and in embodiments of the invention the layer of preferentially functionalizable material 231 is disposed on the second electrode 220. The presence or absence of the first layer of dielectric material 235 in the device of FIG. 2 can depend on factors, such as the adhesion between the material that the second electrode is comprised of and the material that the preferentially functionalizable material 231 is comprised of. The layer of preferentially functionalizable material 231 is a material that can bind or attach linker molecules and/or biomolecules of interest preferentially as compared to the ability of the materials that comprise the exposed regions of the nanogap (surface regions that under operational conditions come into contact with liquids) transducer to bind or attach linker molecules or biomolecules of interest. In embodiments of the invention, the layer of preferentially functionalizable material 231 is comprised of silicon dioxide, and the first and the second layers of dielectric material 235 and 240 are comprised of silicon oxynitride. The exposed silicon dioxide region (molecular binding region 230) can be preferentially functionalized using a silane, such as, for example, aminopropyltriethoxysilane, when the electrodes 215 and 220 are comprised of platinum, palladium, gold, carbon materials (for example, diamond, graphitic carbon, or amorphous carbon), nickel, and/or indium tin oxide. In additional embodiments of the invention, the layer of preferentially functionalizable material 231 is comprised of hafnium oxide, aluminum oxide, or tantalum oxide and can be preferentially functionalized using a silane, such as, for example, aminopropyltriethoxysilane, when the electrodes 215 and 220 are comprised of platinum, palladium, gold, carbon materials (for example, diamond, graphitic carbon, or amorphous carbon), nickel, and/or indium tin oxide. In additional embodiments of the invention, the preferentially functionalizable layer 231 is comprised gold, platinum, or palladium, and the resulting molecular binding region 230 can be preferentially functionalized with molecules comprising a thiol (—SH) or disulfide (—S—S—) group, when the electrodes 215 and 220 are comprised of carbon materials, such as diamond, graphitic carbon, or amorphous carbon. Other materials for the preferentially functionalizable material 231 and dielectric layers 235 and 240 are also possible.

In embodiments of the invention, the molecular binding region 230 comprises a linker molecule, a combination of linker molecules, and/or a probe molecule. Linker molecules can be attached to the surface of the molecular binding region 230 and comprise a functional group that is capable of attaching to a molecule of interest (for example, a probe molecule or an additional linker molecule). Linker molecules can be chosen to selectively react with the molecular binding region 230 (but not with dielectric materials 235 and 240 or the electrode materials 215 and 220), and include molecules such as, for example, silanes, thiols, disulfides, isothiocynates, alkenes, and alkynes. Probe molecules are molecules that can selectively bind a target molecule of interest, such as, for example, sequences of DNA, sequences of RNA, biotin or avidin, and antibodies, antigens, receptors and their specific binding partners, proteins and their specific small molecule binding partners, and/or peptides. Probe molecules comprise one or more molecular recognition sites. Antibodies include, for example, polyclonal and monoclonal antibodies, as well as antigen binding fragments of such antibodies. An antibody or an antigen binding fragment of an antibody is characterized, for example, by having specific binding activity for an epitope of an analyte. The probe can be either member of a specific binding pair, such as, for example, immunological pairs such as antigen-antibody, biotin-avidin, hormones-hormone receptors, nucleic acid duplexes, IgG-protein A, and polynucleotide pairs such as DNA-DNA, and DNA-RNA. Probe molecules can be coupled to linker molecules through known coupling chemistries.

The electrodes 215 and 220 are comprised of a conducting material. In embodiments of the invention, electrodes 215 and 220 are comprised of diamond, platinum, and/or gold. In additional embodiments of the invention, the electrodes 215 and 220 are comprised of palladium, nickel, graphitic carbon, amorphous carbon, and/or indium tin oxide. In embodiments of the invention, at least one electrode 215 or 220 is comprised of a conducting diamond material. In embodiments of the invention, electrode 215 is comprised of conducting diamond. In further embodiments of the invention, both electrodes 215 and 220 are comprised of conducting diamond material. Diamond can be made to conduct electricity by doping it, for example. Dopants include, for example, boron, nitrogen, and phosphorous. In an embodiment of the invention, the dopant is boron. Doping concentrations for boron doped diamond materials include concentrations greater than $10^{20}$ atoms/cm$^3$ and less than $10^{22}$ atoms/cm$^3$. In embodiments of the invention, when the first electrode 215 is comprised of a conducting diamond material, the height of the electrode, $h_2$, is between 200 and 1000 nm. In alternate embodiments, the height of the conducting diamond electrode, $h_2$, is between 5 and 25 nm. In embodiments of the invention, the conducting diamond film is microcrystalline or nanocrystalline diamond. In operation, typically a reference electrode (not shown) is also used with the nanogap transducer. The reference electrode is in contact with the solution which is being measured but does not have to be located within the nanogap.

Figure 3:
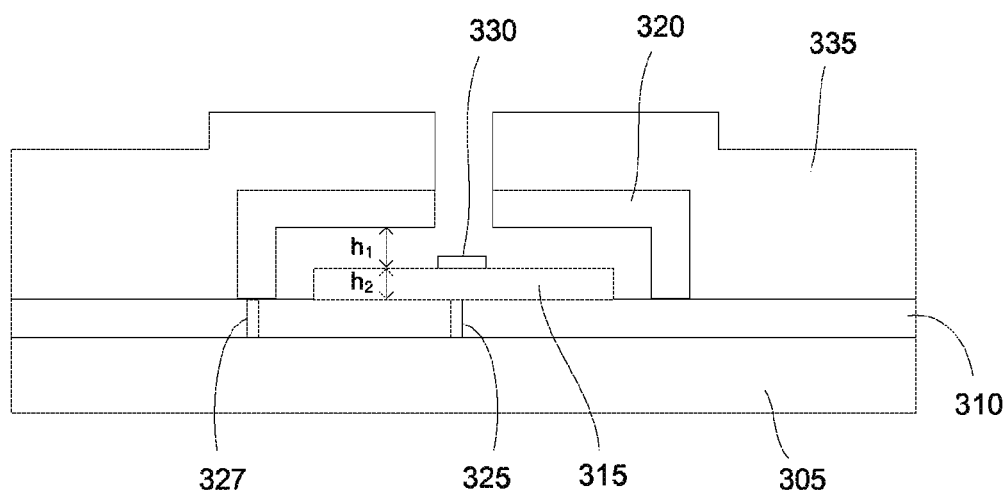
FIG. 3 is a schematic diagram illustrating an additional embodiment of a nanogap transducer.

FIG. 3 illustrates an additional nanogap transducer that is capable of functioning as an electronic sensor, detecting redox molecules, and/or functioning as a redox cycline sensor. In FIG. 3, a substrate 305 has a dielectric layer 310 and first electrode 315. A second electrode 320 is separated from the first electrode by a gap that has a height, $h_1$. In embodiments of the invention, the height of the gap, $h_1$, is less than 500 nm or between 10 and 200 nm, between 10 and 150 nm, or between 25 and 150 nm. Optional electronic interconnections 325 and 327, such as vias through dielectric layer 310, make connections to optional electronics (not shown) housed in the substrate 305. In embodiments of the invention, the substrate 305 is an integrated circuit (IC) chip and comprises electronics for, for example, driving electrodes 315 and 320, signal reading, signal amplification, and/or data output. The substrate can be other materials, such as, for example, glass, passivated metal, polymer, semiconductor, PDMS (polydimethylsiloxane), and/or flexible elastomeric substances. In embodiments in which the substrate does not house electronics, electrical connections to electrodes 315 and 320 can extend out along a surface of insulating layer 310 or through substrate 305, although other configurations are also possible.

The nanogap transducer of FIG. 3 comprises a molecular binding region 330 that is disposed on electrode 315. The molecular binding region 330 is comprised of preferentially functionalizable material. The preferentially functionalizable material is a material that can bind or attach linker molecules and/or biomolecules of interest preferentially as compared to the ability of the materials that comprise the exposed regions of the nanogap transducer (surface regions that under operational conditions come into contact with liquids) to bind or attach linker molecules or biomolecules of interest. In embodiments of the invention, the region of preferentially functionalizable material 330 is comprised of silicon dioxide, and second layer of dielectric material 335 is comprised of silicon oxynitride. The exposed silicon dioxide region (molecular binding region 330) can be preferentially functionalized using a silane, such as, for example, aminopropyltriethoxysilane, when the electrodes 315 and 320 are comprised of platinum, palladium, gold, carbon materials (for example, diamond, graphitic carbon, or amorphous carbon), nickel, and/or indium tin oxide. In additional embodiments of the invention, the molecular binding region 330 is comprised of hafnium oxide, aluminum oxide, or tantalum oxide and can be preferentially functionalized using a silane, such as, for example, aminopropyltriethoxysilane, when the electrodes 315 and 320 are comprised of platinum, palladium, gold, carbon materials (for example, diamond, graphitic carbon, or amorphous carbon), nickel, and/or indium tin oxide. In additional embodiments of the invention, the molecular binding region 330 is comprised, gold, platinum, or palladium, and can be preferentially functionalized with molecules comprising a thiol (—SH) or disulfide (—S—S—) group, when the electrodes 315 and 320 are comprised of carbon materials, such as diamond, graphitic carbon, or amorphous carbon. Other materials for the preferentially functionalizable material 330 and dielectric layer 335 are also possible.

In embodiments of the invention, the molecular binding region 330 has an available surface area (the surface area that capable of being exposed to solution within the nanogap cavity and capable of binding a molecule) that can accommodate the binding of only one desired molecule. In embodiments of the invention, the molecular binding region 330 has an available surface area of 40 nm$^2$ to 500,000 nm$^2$. The size of the molecular binding region 330 employed can depend on factors such as the size of the linker molecule used. A large linker molecule can allow a larger sized molecular binding region 330 because the size of the linker molecule can limit the number of binding sites on the molecular binding region 330. In alternate embodiments, the number of molecular attachment reactions at the molecular binding region 330 can be limited by solution concentration of the linker molecule and/or probe molecule during attachment to the molecular binding regions 330 of an array of nanogap transducers. For an essentially 100% yield for attachment to the molecular binding regions 330, only a percentage of the nanogap tranducers may have only one molecule attached to the molecular binding region 330 while the remaining transducers have more than one molecule attached to the molecular binding region 330. The number of molecules per molecular binding region 330 can be determined by testing prior to use and/or by filtering results that axe not consistent with a single molecule in the molecular binding region 330.

In embodiments of the invention, the molecular binding region 330 comprises a linker molecule, a combination of linker molecules, and/or a probe molecule. Linker molecules can be attached to the surface of the molecular binding region 330 and comprise a functional group that is capable of attaching to a molecule of interest (for example, a probe molecule or an additional linker molecule). Linker molecules can be chosen to selectively react with the molecular binding region 330 (but not with dielectric material 335 or the electrode materials 315 and 320), and include molecules such as, for example, silanes, thiols, disulfides, isothiocynates, alkenes, and alkynes. Probe molecules are molecules that can selectively bind a target molecule of interest, such as, for example, sequences of DNA, sequences of RNA, biotin or avidin, and antibodies, receptors and their specific binding partners, proteins and their specific small molecule binding partners, and/or peptides. Probe molecules comprise one or more molecular recognition sites. Antibodies include, for example, polyclonal and monoclonal antibodies, as well as antigen binding fragments of such antibodies. An antibody or an antigen binding fragment of an antibody is characterized, for example, by having specific binding activity for an epitope of an analyte. The probe can be either member of a specific binding pair, such as, for example, immunological pairs such as antigen-antibody, biotin-avidin, hormones-hormone receptors, nucleic acid duplexes, IgG-protein A, and polynucleotide pairs such as DNA-DNA, and DNA-RNA. Probe molecules can be coupled to linker molecules through known coupling chemistries.

The electrodes 315 and 320 are comprised of a conducting material. In embodiments of the invention, electrodes 315 and 320 are comprised of diamond, platinum, and/or gold. In additional embodiments of the invention, the electrodes 315 and 320 are comprised of palladium, nickel, graphitic carbon, amorphous carbon, and/or indium tin oxide. In embodiments of the invention, at least one electrode 315 or 320 is comprised of a conducting diamond material. In embodiments of the invention, electrode 315 is comprised of conducting diamond. In further embodiments of the invention, both electrodes 315 and 320 are comprised of conducting diamond material. Diamond can be made to conduct electricity by doping it, for example. Dopants include, for example, boron, nitrogen, and phosphorous. In an embodiment of the invention, the dopant is boron. Doping concentrations for boron doped diamond materials include concentrations greater than $10^{20}$ atoms/cm$^3$ and less than $10^{22}$ atoms/cm$^3$. In embodiments of the invention, when the first electrode 315 is comprised of a conducting diamond material, the height of the electrode, $h_2$, is between 200 and 1000 nm, In alternate embodiments, the height of the conducting diamond electrode, $h_2$, is between 5 and 25 nm. In embodiments of the invention, the conducting diamond film is microcrystalline or nanocrystalline diamond. In operation, typically a reference electrode (not shown) is also used with the nanogap transducer. The reference electrode is in contact with the solution which is being measured but does not have to be located within the nanogap.

Figure 4:
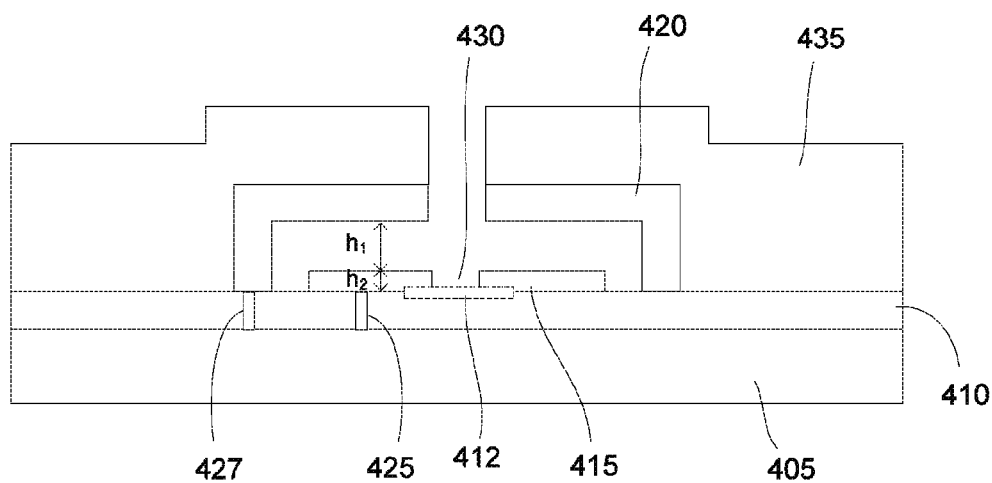
FIG. 4 is a schematic diagram illustrating an additional embodiment of a nanogap transducer.

FIG. 4 illustrates a further additional nanogap transducer that is capable of functioning as an electronic sensor, detecting redox molecules, and/or functioning as a redox cycling sensor. In FIG. 4, a substrate 405 has a dielectric layer 410 and first electrode 415. A second electrode 420 is separated from the first electrode by a gap that has a height, $h_1$. In embodiments of the invention, the height of the gap, $h_1$, is less than 500 nm or between 10 and 200 nm, between 10 and 150 nm, or between 25 and 150 nm. Optional electronic interconnections 425 and 427, such as vias through dielectric layer 410, make connections to optional electronics (not-shown) housed in the substrate 405. In embodiments of the invention, the substrate 405 is an integrated circuit (IC) chip and comprises electronics for, for example, driving electrodes 415 and 420, signal reading, signal amplification, and/or data output. The substrate can be other materials, such as, for example, glass, passivated metal, polymer, semiconductor, PDMS (polydimethylsiloxane), and/or flexible elastomeric substances. In embodiments in which the substrate does not house electronics, electrical connections to electrodes 415 and 420 can extend out along a surface of insulating layer 410 or through substrate 405, although other configurations are also possible.

The nanogap transducer of FIG. 4 comprises a molecular binding region 430 that is disposed in a hole in electrode 415. The molecular binding region 430 is comprised of a preferentially functionalizable material. The preferentially functionalizable material is a material that can bind or attach linker molecules and/or biomolecules of interest preferentially as compared to the ability of the materials that comprise the exposed regions of the nanogap transducer (surface regions that under operational conditions come into contact with liquids) to bind or attach linker molecules or biomolecules of interest. The molecular binding region 430 can comprise an exposed region of the dielectric layer 410 or an optional region 412 of preferentially functionalizable material that is different from the dielectric layer 410. The optional region of preferentially functionalizable material 412 is located proximate to the hole in the first electrode 415 and a surface of the region of preferentially functionalizable material 412 is exposed through the hole in the electrode. Optional region 412 comprising preferentially functionalizable material can have other shapes and sizes and be recessed within dielectric region 410 or on a surface of dielectric region 410. In embodiments of the invention, the region of preferentially functionalizable material 430 is comprised of silicon dioxide and the second layer of dielectric material 435 is comprised of silicon oxynitride. The exposed silicon dioxide region (molecular binding region 430) can be preferentially functionalized using a silane, such as, for example, aminopropyltriethoxysilane, when the electrodes 415 and 420 are comprised of platinum, palladium, gold, carbon materials (for example, diamond, graphitic carbon, or amorphous carbon), nickel, and/or indium tin oxide. In additional embodiments of the invention, the molecular binding region 430 is comprised of hafnium oxide, aluminum oxide, or tantalum oxide and can be preferentially functionalized using a silane, such as, for example, aminopropyltriethoxysilane, when the electrodes 415 and 420 are comprised of platinum, palladium, gold, carbon materials (for example, diamond, graphitic carbon, or amorphous carbon), nickel, and/or indium tin oxide. In additional embodiments of the invention, the molecular binding region 430 is comprised gold, platinum, or palladium, and can be preferentially functionalized with molecules comprising a thiol (—SH) or disulfide (—S—S—) group, when the electrodes 415 and 420 are comprised of carbon materials, such as diamond, graphitic carbon, or amorphous carbon. Other materials for the preferentially functionalizable material 430 and dielectric layer 435 are also possible.

In embodiments of the invention, the molecular binding region 430 has an available surface area (the surface area that capable of being exposed to solution within the nanogap cavity and capable of binding a molecule) that can accommodate the binding of only one desired molecule. In embodiments of the invention, the molecular binding region 430 has an available surface area of 40 nm$^2$ to 500,000 nm$^2$. The size of the molecular binding region 430 employed can depend on factors such as the size of the linker molecule used. A large linker molecule can allow a larger sized molecular binding region 430 because the size of the linker molecule can limit the number of binding sites on the molecular binding region 430. In alternate embodiments, the number of molecular attachment reactions at the molecular binding region 430 can be limited by solution concentration of the linker molecule and/or probe molecule during attachment to the molecular binding regions 430 of an array of nanogap transducers. For an essentially 100% yield for attachment to the molecular binding regions 430, only a percentage of the nanogap tranducers may have only one molecule attached to the molecular binding region 430 while the remaining transducers have more than one molecule attached to the molecular binding region 430. The number of molecules per molecular binding region 330 can be determined by testing prior to use and/or by filtering results that are not consistent with a single molecule in the molecular binding region 430.

In embodiments of the invention, the molecular binding region 430 comprises a linker molecule, a combination of linker molecules, and/or a probe molecule. Linker molecules can be attached to the surface of the molecular binding region 430 and comprise a functional group that is capable of attaching to a molecule of interest (for example, a probe molecule or an additional linker molecule). Linker molecules can be chosen to selectively react with the molecular binding region 430 (but not with dielectric material 435 or the electrode materials 415 and 420), and include molecules such as, for example, silanes, thiols, disulfides, isothiocynates, alkenes, and alkynes. Probe molecules are molecules that can selectively bind a target molecule of interest, such as, for example, sequences of DNA, sequences of RNA, biotin or avidin, and antibodies, receptors and their specific binding partners, proteins and their specific small molecule binding partners, and/or peptides. Probe molecules comprise one or more molecular recognition sites. Antibodies include, for example, polyclonal and monoclonal antibodies, as well as antigen binding fragments of such antibodies. An antibody or an antigen binding fragment of an antibody is characterized, for example, by having specific binding activity for an epitope of an analyte. The probe can be either member of a specific binding pair, such as, for example, immunological pairs such as antigen-antibody, biotin-avidin, hormones-hormone receptors, nucleic acid duplexes, IgG-protein A, and polynucleotide pairs such as DNA-DNA, and DNA-RNA. Probe molecules can be coupled to linker molecules through known coupling chemistries.

The electrodes 415 and 420 are comprised of a conducting material. In embodiments of the invention, the electrodes 415 and 420 are comprised of diamond, platinum, and/or gold. In additional embodiments of the invention, the electrodes 415 and 420 are comprised of palladium, nickel, graphitic carbon, amorphous carbon, and/or indium tin oxide. In embodiments of the invention, at least one electrode 415 or 420 is comprised of a conducting diamond material. In embodiments of the invention, electrode 415 is comprised of conducting diamond. In further embodiments of the invention, both electrodes 415 and 420 are comprised of conducting diamond material. Diamond can be made to conduct electricity by doping it, for example. Dopants include, for example, boron, nitrogen, and phosphorous. In an embodiment of the invention, the dopant is boron. Doping concentrations for boron doped diamond materials include concentrations greater than $10^{20}$ atoms/cm$^3$ and less than $10^{22}$ atoms/cm$^3$. In embodiments of the invention, when the first electrode 415 is comprised of a conducting diamond material, the height of the electrode, $h_2$, is between 200 and 1000 nm. In alternate embodiments, the height of the conducting diamond electrode, $h_2$, is between 5 and 25 nm. In embodiments of the invention, the conducting diamond film is microcrystalline or nanocrystalline diamond. In operation, typically a reference electrode (not shown) is also used with the nanogap transducer. The reference electrode is in contact with the solution which is being measured but does not have to be located within the nanogap.

Figure 5A:
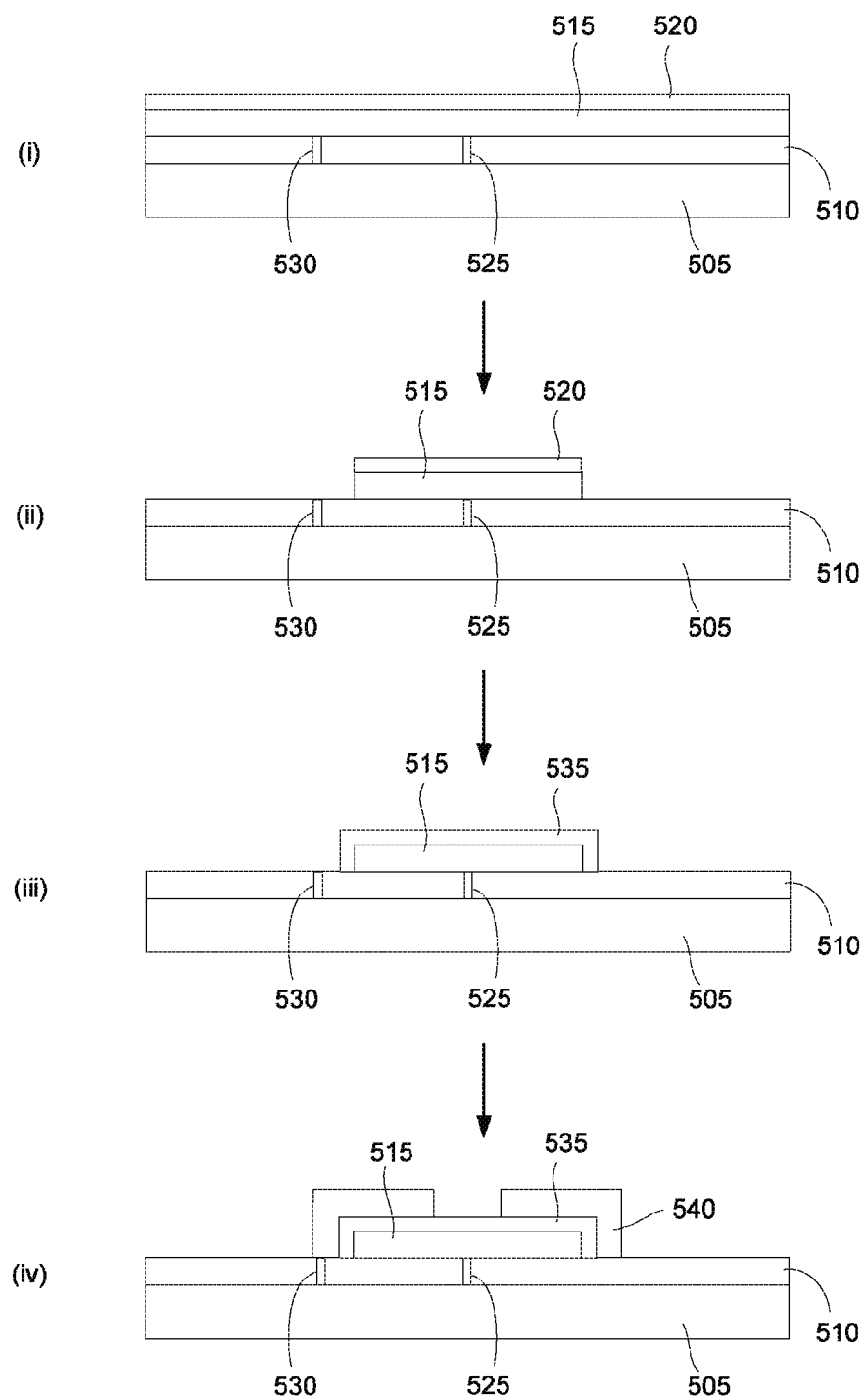
FIGS. 5A-B diagram a method for making a nanogap transducer.
Figure 5B:
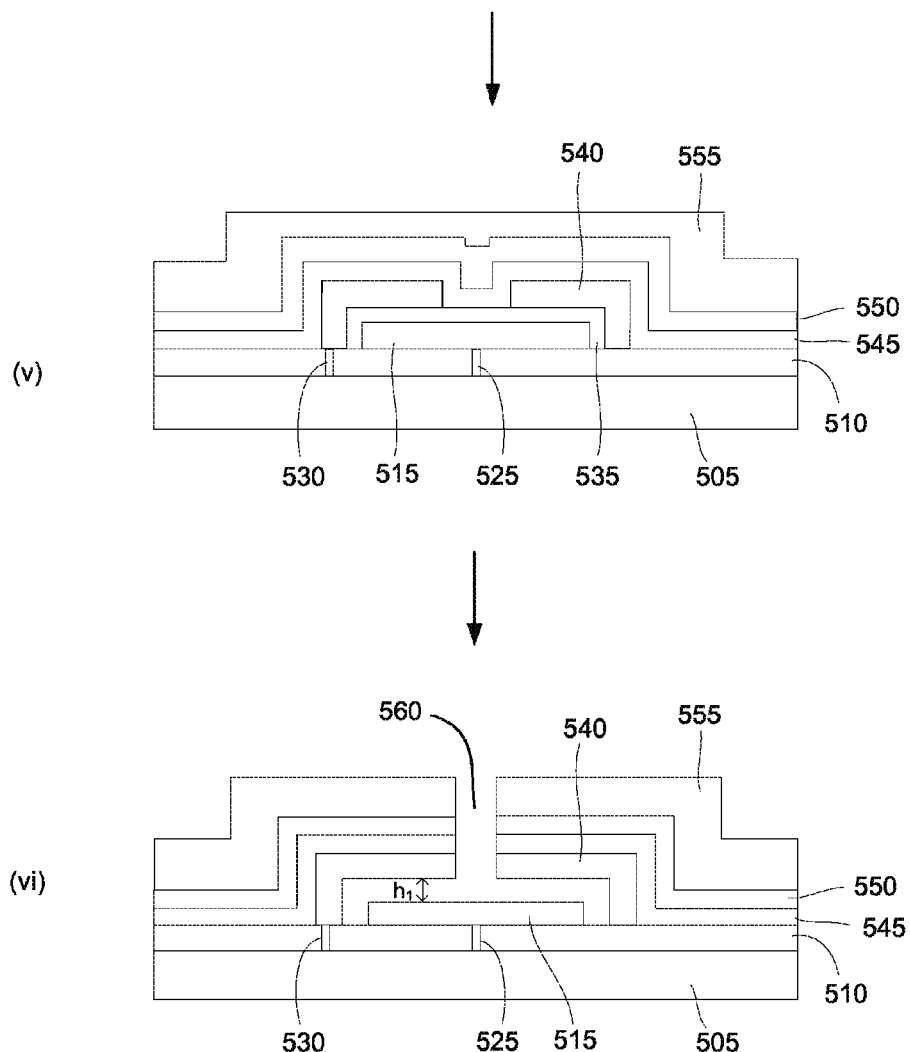

FIGS. 5A-B illustrate a method for making a nanogap transducer having a molecular binding region. In FIG. 5A, structure (i) comprises a substrate 505, a dielectric layer 510, and a first electrode layer 515. In embodiments of the invention, the first electrode layer 515 is comprised of a conducting diamond material, platinum, gold, palladium, nickel, graphitic carbon, amorphous carbon, or indium tin oxide. In the embodiment in which the first electrode layer 515 is comprised of conducting diamond, a hard mask layer 520 is disposed on the first electrode layer 515. The conducting diamond material can be deposited, for example, using a hot filament CVD (chemical vapor deposition), a microwave plasma CVD, or a combustion flame assisted CVD process. The conducting diamond material can be deposited on a seed layer wherein the seed layer is deposited, for example by immersing the substrate in a solution that comprises diamond particles and attaching the particles to the surface using ultrasonication or by suspending diamond particles in a material that is spun onto the substrate surface. In embodiments of the invention, the conducting diamond material is boron doped diamond. In embodiments of the invention, the conducting diamond material is deposited with a boron doping concentration of greater than $10^{20}$ atoms/cm$^3$ and less than $10^{22}$ atoms/cm$^3$. In embodiments of the invention, the hard mask layer 520 is comprised of, for example, chromium or silicon dioxide. In embodiments of the invention, in which the first electrode layer 515 is comprised of platinum and/or gold, the platinum and/or gold can be deposited by sputtering and patterned using a liftoff process in which a photoresist layer is deposited and patterned before the platinum and/or gold is deposited and then the photoresist is lifted off to remove the platinum and/or gold in unwanted areas. In embodiments of the invention, the substrate 505 is, for example, an IC chip comprising electronics for, for example, driving electrodes, signal detection, signal amplification, and/or data output. Optionally, conducting vias 525 and 530 are provided through the dielectric layer 510 to the substrate 505 that interconnect the electrodes with the optional electronics housed in the substrate 505. Other materials are also possible for substrate 505.

In embodiments of the invention, when the first electrode 515 is comprised of a conducting diamond material, it was found that it can be desirable to minimize the thickness of the first electrode in order to minimize the probability of shorting between the top and bottom electrodes. High aspect ratios for the first electrode were found to cause thinning of the sacrificial conformal coating at the edges of the electrode. However, it was also found that a minimum electrode height for the first electrode was necessary for microcrystalline diamond materials to avoid excessive surface roughness. It was found that excessive surface roughness of the first electrode could also cause openings in the sacrificial conformal coating and shorting between the first and the second electrodes. The height of the first electrode, when the first electrode is comprised of conducting diamond, in embodiments of the invention, can be between 200 and 1000 nm, between 300 and 800 nm, between 350 and 700 nm in order to balance height minimization with surface roughness considerations.

Structure (ii) of FIG. 5A can be created by patterning the hard mask layer 520, removing the hard mask layer 520 in unwanted regions, and etching the exposed diamond electrode layer 515. The exposed diamond electrode layer 515 can be etched, for example, using an oxygen plasma. An elevated temperature, such as between 70 and 100 C, can facilitate the oxygen plasma etch. The hard mask layer 520 is then removed.

A conformal film of a sacrificial material 535 is deposited and patterned creating structure (iii) of FIG. 5A. The conformal film of sacrificial material 535 can be patterned by first depositing a photoresist, patterning the photoresist, depositing the sacrificial material, for example, by sputtering or atomic layer deposition (ALD), and lifting off the photoresist to define the conformal film, of sacrificial material in the desired regions (a liftoff process). In embodiments of the invention, the sacrificial material comprises chromium or tungsten. The conformal film of sacrificial material 535 can be deposited, for example, by sputtering ALD deposition to achieve a film that wraps around the bottom electrode 515. In embodiments of the invention, the thin film of sacrificial material 535 has a thickness of less than 500 nm or between 10 and 200 nm, between 10 and 150 nm, or between 25 and 150 nm.

A second electrode material 540 is deposited on the conformal layer of sacrificial material 535 and patterned creating structure (iv) of FIG. 5A. The second electrode material 540 can be patterned lithographically using a liftoff process. In embodiments of the invention, the second electrode material 540 is conducting diamond. Conducting diamond can be deposited, for example, by seeding and then depositing the layer using a hot filament CVD, a microwave plasma CVD, or a combustion flame assisted CVD process. In embodiments of the invention, when the second electrode 540 material is diamond, the conformal film of sacrificial material 535 comprises tungsten. In further embodiments of the invention, the second electrode 540 is comprised of platinum, gold, nickel, palladium, graphitic carbon, amorphous carbon, or indium tin oxide. The platinum electrode can be deposited, for example, by sputtering a thin layer of chromium (which can be about 10 nm thick) as an adhesion layer and then sputtering a layer of platinum. The gold electrode material can be deposited, for example, by sputtering, evaporation, electrodeposition, or electroless deposition processes. In embodiments of the invention, the sacrificial material 535 is tungsten when the second electrode 540 is comprised of gold.

A second dielectric layer 545, a layer of preferentially functionalizable material 550, and a third layer of dielectric material 555 are then deposited on the structure (iv) of FIG. 5A, yielding structure (v) of FIG. 5B. The dielectric material of the second and third layers 545 and 555 can be, for example, silicon oxynitride, and the preferentially functionalizable material layer 550 can be silicon dioxide. In alternate embodiments, the dielectric material of the second and third layers 545 and 555 can be, for example, silicon nitride, and the preferentially functionalizable material layer 550 can be gold, platinum, or palladium. An access hole 560 is created through the second dielectric layer 545, the layer of preferentially functionalizable material 550, and the third layer of dielectric material 555. The access hole 560 can be created by defining a hole lithographically using a photoresist mask and then using a dry etching process to make the hole. The sacrificial material 535 is removed creating the gap between the first and second electrodes 515 and 540. The sacrificial material 535 can be removed using a wet etch, for example, in the embodiments in which the sacrificial material 535 is tungsten or chromium. The resulting structure is shown in FIG. 5B (vi). In embodiments of the invention, the height of the gap, $h_1$, is less than 500 nm or between 10 and 200 nm, between 10 and 150 nm, or between 25 and 150 nm.

Figure 6A:
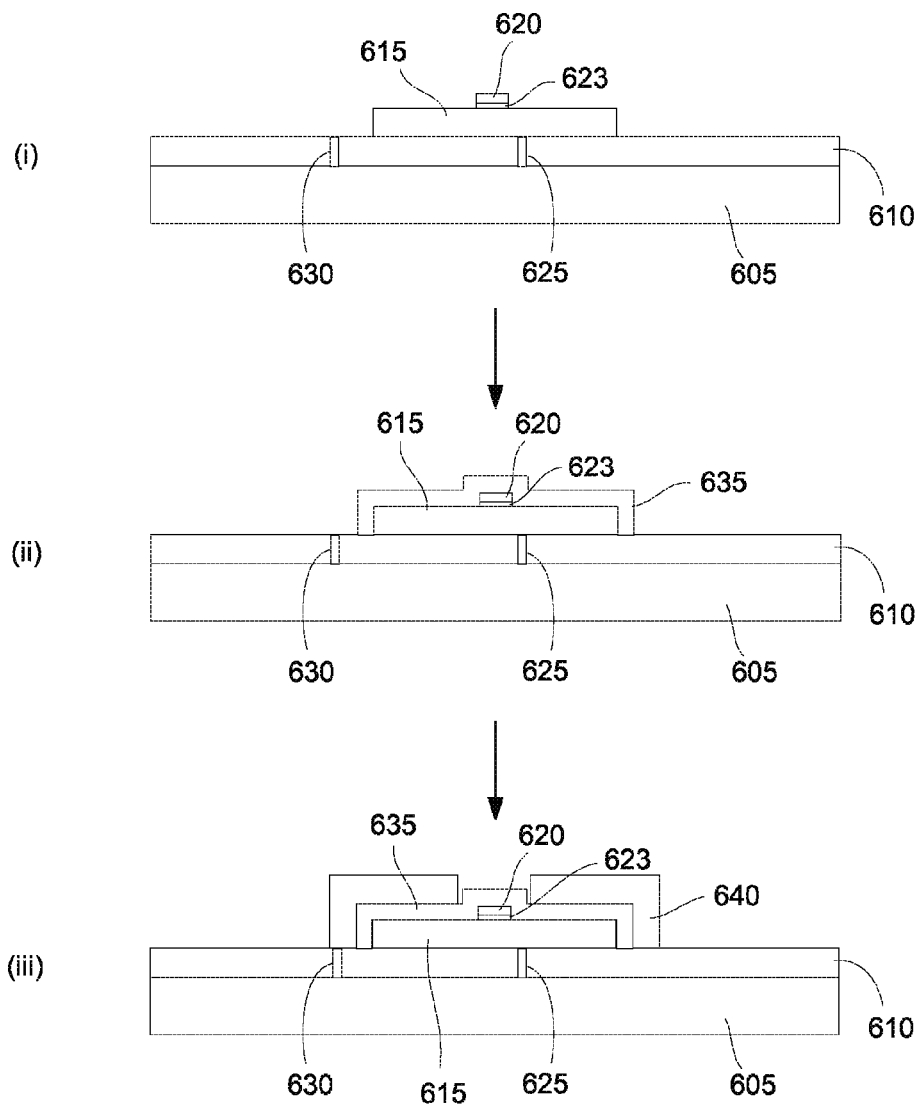
FIGS. 6A-B diagram an additional method for making a nanogap transducer.
Figure 6B:
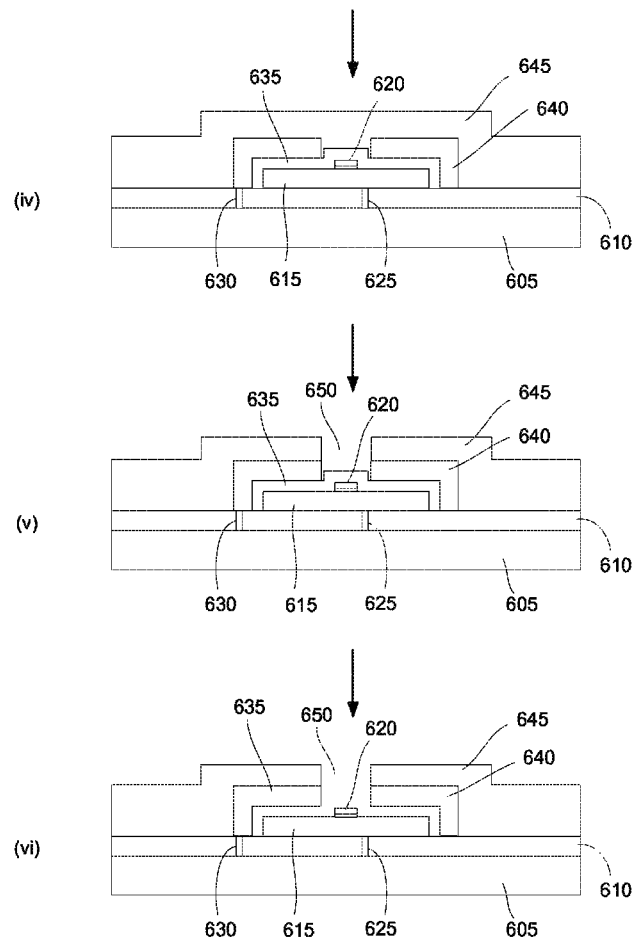

FIGS. 6A-B illustrate an additional method for making a nanogap transducer having a molecular binding region. In FIG. 6A, structure (i) comprises a substrate 605, a dielectric layer 610, and a first electrode 615. In embodiments of the invention, the first electrode 615 is comprised of a conducting diamond material, platinum, gold, palladium, nickel, graphitic carbon, amorphous carbon, or indium tin oxide. In embodiments of the invention, the conducting diamond material is boron doped diamond. In embodiments of the invention, the conducting diamond material is deposited with a boron doping concentration of greater than $10^{20}$ atoms/cm$^3$ and less than $10^{22}$ atoms/cm$^3$. In embodiments of the invention, the substrate 605 is, for example, an IC chip comprising electronics for, for example, driving electrodes, signal detection, signal amplification, and/or data output. Optionally, conducting vias 625 and 630 are provided through the dielectric layer 610 to the substrate 605 that interconnect the electrodes with the optional electronics housed in the substrate 605. Other materials are also possible for substrate 605. A molecular binding region 620 comprised of a preferentially functionalizable material is deposited on the first electrode 615. Optionally, an adhesive layer 623 is between the the molecular binding region 620 and the electrode 615. The adhesive layer 623 is comprised of silicon nitride and can be deposited by CVD. The molecular binding regions 620 can be, for example, deposited by CVD and patterned by photolithography. In embodiments of the invention, the molecular binding region 620 has an exposed surface area of between 40 nm$^2$ and 500,000 nm$^2$.

In embodiments of the invention, when the first electrode 615 is comprised of a conducting diamond material, it was found that it can be desirable to minimize the thickness of the first electrode in order to minimize the probability of shorting between the top and bottom electrodes. High aspect ratios for the first electrode were found to cause thinning of the sacrificial conformal coating at the edges of the electrode. However, it was also found that a minimum electrode height for the first electrode was necessary for microcrystalline diamond materials to avoid excessive surface roughness. It was found that excessive surface roughness of the first electrode could also cause openings in the sacrificial conformal coating and shorting between the first and the second electrodes. The height of the first electrode, when the first electrode is comprised of conducting diamond, in embodiments of the invention, can be between 200 and 1000 nm, between 300 and 800 nm, between 350 and 700 nm in order to balance height minimization with surface roughness considerations.

Structure (ii) of FIG. 6A can be created by depositing and patterning a conformal film of a sacrificial material 635 on the structure (i) of FIG. 6A. The conformal film of sacrificial material 635 can be patterned by first depositing a photoresist, patterning the photoresist, depositing the sacrificial material, for example, by sputtering or atomic layer deposition (ALD), and lifting off the photoresist to define the conformal film of sacrificial material in the desired regions (a liftoff process). In embodiments of the invention, the sacrificial material comprises chromium or tungsten. The conformal film of sacrificial material 635 can be deposited, for example, by sputtering ALD deposition to achieve a film that wraps around the bottom electrode 615. In embodiments of the invention, the thin film of sacrificial material 635 has a thickness of less than 500 nm or between 10 and 200 nm, between 10 and 150 nm, or between 25 and 150 nm.

A second electrode 640 material is deposited on the conformal layer of sacrificial material 635 and patterned creating structure (iii) of FIG. 6A. The second electrode 640 material can be patterned lithographically using a liftoff process. In embodiments of the invention, the second electrode 640 material is conducting diamond. Conducting diamond can be deposited, for example, by seeding and then depositing the layer using a hot filament CVD, a microwave plasma CVD, or a combustion flame assisted CVD process. In embodiments of the invention, when the second electrode 640 material is diamond, the conformal film of sacrificial material 635 comprises tungsten. In further embodiments of the invention, the second electrode 640 is comprised of platinum, gold, nickel, palladium, graphitic carbon, amorphous carbon, or indium tin oxide. The platinum electrode can be deposited, for example, by sputtering a thin layer of chromium (which can be about 10 nm thick) as an adhesion layer and then sputtering a layer of platinum. The gold electrode material can be deposited, for example, by sputtering, evaporation, electrodeposition, or electroless deposition processes. In embodiments of the invention, the sacrificial material 635 is tungsten when the second electrode 640 is comprised of gold.

A second dielectric layer 645 is then deposited on the structure (iii) of FIG. 6A, yielding structure (iv) of FIG. 6B. The dielectric material of the second layer 645 can be, for example, silicon oxynitride, and the preferentially functionalizable material of the molecular binding region 620 can be silicon dioxide. In alternate embodiments, the dielectric material of the second layer 645 can be, for example, silicon dioxide, silicon nitride, or silicon oxynitride, and the preferentially functionalizable material can be gold, platinum or palladium. An access hole 650 is created through the second dielectric layer 645 creating structure (v) of FIG. 6B. The access hole 650 can be created by defining a hole lithographically using a photoresist mask and then using a dry etching process to make the hole. The sacrificial material 635 is removed creating the gap between the first and second electrodes 615 and 640. The sacrificial material 635 can be removed using a wet etch, for example, in the embodiments in which the sacrificial material 635 is tungsten or chromium. The resulting structure is shown in FIG. 6B (vi). In embodiments of the invention, the height of the gap between the first and the second electrodes 615 and 640 is less than 500 nm or between 10 and 200 nm, between 10 and 150 nm, or between 25 and 150 nm.

Figure 7A:
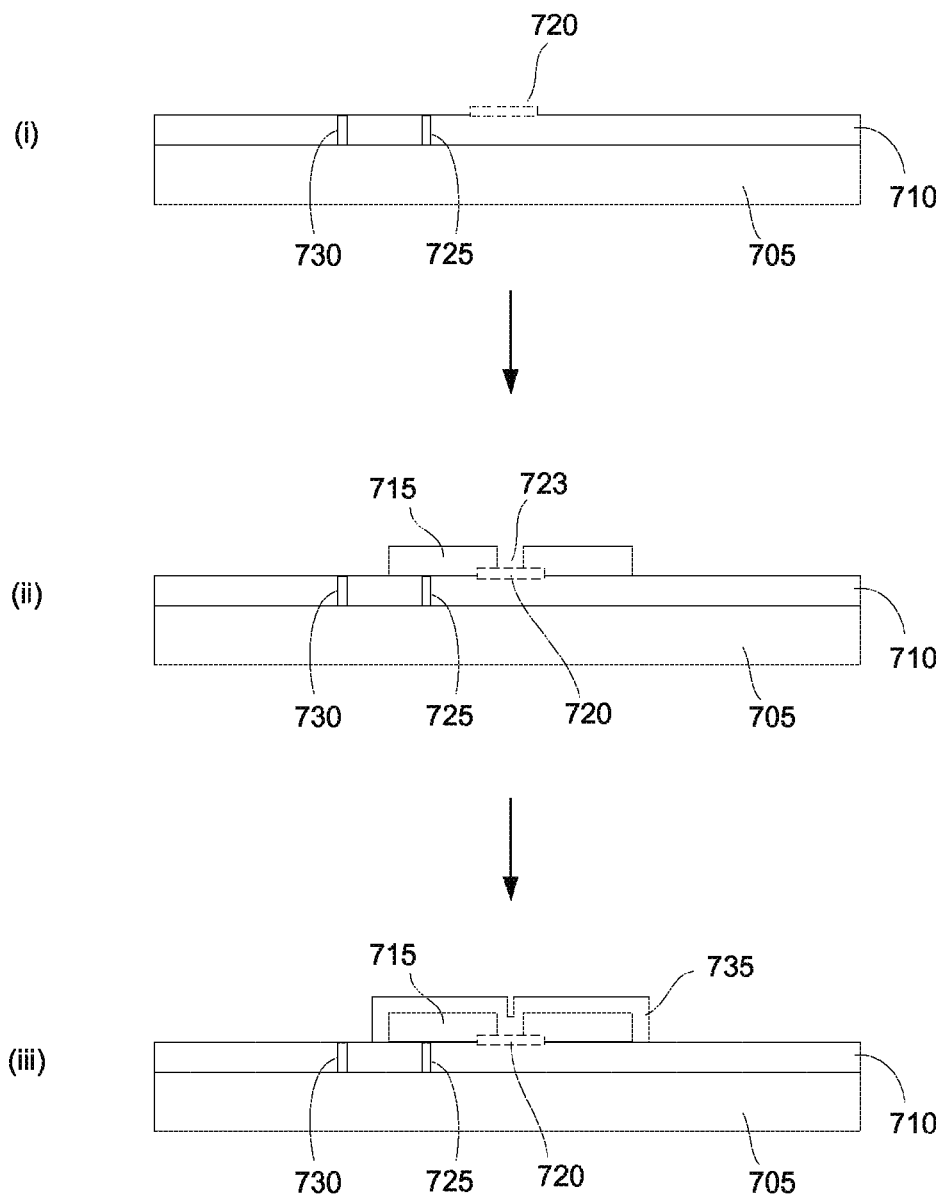
FIGS. 7A-B diagram an additional method for making a nanogap transducer.
Figure 7B:
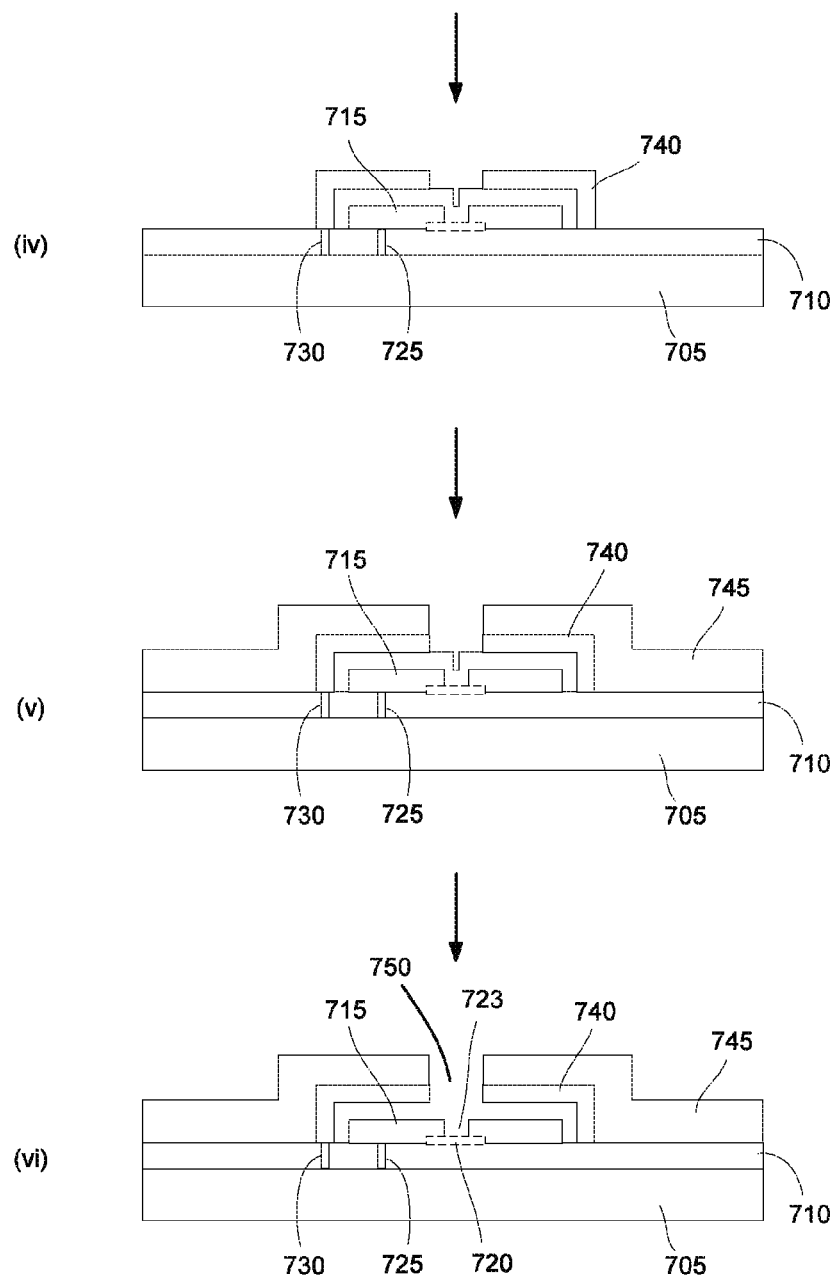

FIGS. 7A-B illustrate a further additional method for making a nanogap transducer having a molecular binding region. In FIG. 7A, structure (i) comprises a substrate 705, a dielectric layer 710, and an optional region of preferentially functionalizable material 720. In embodiments of the invention, the substrate 705 is, for example, an IC chip comprising electronics for, for example, driving electrodes, signal detection, signal amplification, and/or data output. Optionally, conducting vias 725 and 730 are provided through the dielectric layer 710 to the substrate 705 that interconnect the electrodes with the optional electronics housed in the substrate 705. Other materials are also possible for substrate 705.

Structure (ii) of FIG. 7A can be created by depositing and patterning a first electrode 715 material. The patterning creates a hole within the first electrode 715 where the molecular binding region 723 is exposed. In embodiments of the invention, the molecular binding region 723 has an exposed surface area of between 40 nm$^2$ and 500,000 nm$^2$. In embodiments of the invention, the first electrode 715 comprised of a conducting diamond material, platinum, gold, nickel, palladium, graphitic carbon, amorphous carbon, or indium tin oxide. In embodiments of the invention, the conducting diamond material is boron doped diamond. In embodiments of the invention, the conducting diamond material is deposited with a boron doping concentration of greater than $10^{20}$ atoms/cm$^3$ and less than $10^{22}$ atoms/cm$^3$. Conducting diamond can be deposited, for example, by seeding and then depositing the layer using a hot filament CVD, a microwave plasma CVD, or a combustion flame assisted CVD process. The conducting diamond material can be patterned using a hard mask. A platinum electrode can be deposited, for example, by sputtering. The gold electrode material can be deposited, for example, by sputtering, evaporation, electrodeposition, or electroless deposition processes. A first electrode 715 comprised of platinum or gold can be patterned lithographically using a liftoff process.

In embodiments of the invention, when the first electrode 715 is comprised of a conducting diamond material, it was found that it can be desirable to minimize the thickness of the first electrode in order to minimize the probability of shorting between the top and bottom electrodes. High aspect ratios for the first electrode were found to cause thinning of the sacrificial conformal coating at the edges of the electrode. However, it was also found that a minimum electrode height for the first electrode was necessary for microcrystalline diamond materials to avoid excessive surface roughness. It was found that excessive surface roughness of the first electrode could also cause openings in the sacrificial conformal coating and shorting between the first and the second electrodes. The height of the first electrode, when the first electrode is comprised of conducting diamond, in embodiments of the invention, can be between 200 and 1000 nm, between 300 and 800 nm, between 350 and 700 nm in order to balance height minimization with surface roughness considerations.

Structure (iii) of FIG. 7A can be created by depositing and patterning a conformal film of a sacrificial material 735 on the structure (ii) of FIG. 7A. The conformal film of sacrificial material 735 can be patterned by first depositing a photoresist, patterning the photoresist, depositing the sacrificial material, for example, by sputtering or atomic layer deposition (ALD), and lifting off the photoresist to define the conformal film of sacrificial material in the desired regions (a liftoff process). In embodiments of the invention, the sacrificial material comprises chromium or tungsten. The conformal film of sacrificial material 735 can be deposited, for example, by sputtering ALD deposition to achieve a film that wraps around the bottom electrode 715. In embodiments of the invention, the thin film of sacrificial material 735 has a thickness of less than 500 nm or between 10 and 200 nm, between 10 and 150 nm, or between 25 and 150 nm.

A second electrode material 740 is deposited on the conformal layer of sacrificial material 735 and patterned creating structure (iv) of FIG. 7B. In embodiments of the invention, the second electrode 740 is comprised of conducting diamond, platinum, gold, nickel, palladium, graphitic carbon, amorphous carbon, or indium tin oxide. In embodiments of the invention, the second electrode material is conducting diamond. Conducting diamond can be deposited, for example, by seeding and then depositing the layer using a hot filament CVD, a microwave plasma CVD, or a combustion flame assisted CVD process. The conducting diamond material can be patterned using a hard mask. In embodiments of the invention, when the second electrode 740 material is diamond, the conformal film of sacrificial material 735 comprises tungsten. In further embodiments of the invention, the second electrode 740 is comprised of platinum or gold. The platinum electrode can be deposited, for example, by sputtering a thin layer of chromium (which can be about 10 nm thick) as an adhesion layer and then sputtering a layer of platinum. The gold electrode material can be deposited, for example, by sputtering, evaporation, electrodeposition, or electroless deposition processes. In embodiments of the invention, the sacrificial material 735 is tungsten when the second electrode 740 is comprised of gold. A second electrode 740 comprised of platinum or gold can be patterned lithographically using a liftoff process.

A second dielectric layer 745 is then deposited on the structure (iv) of FIG. 7A, and patterned yielding structure (v) of FIG. 7B. The dielectric material of the second layer 745 can be, for example, silicon oxynitride, and the preferentially functionalizable material of the molecular binding region 723 can be silicon dioxide. In alternate embodiments, the dielectric material of the second layer 745 can be, for example, silicon dioxide, silicon nitride, or silicon oxynitride, and the preferentially functionalizable material can be gold, platinum, or palladium. The patterning creates an access hole 750 through the second dielectric layer 745. The access hole 750 can be created by defining a hole lithographically using a photoresist mask and then using a dry etching process to make the hole. The sacrificial material 735 is removed creating structure (vi) of FIG. 7B. The sacrificial material 735 can be removed using a wet etch, for example, in the embodiments in which the sacrificial material 735 is tungsten or chromium. In embodiments of the invention, the height of the gap between the first and the second electrodes 715 and 740 is less than 500 nm or between 10 and 200 nm, between 10 and 150 nm, or between 25 and 150 nm.

Silane molecules that can be used to modify a surface toward further molecular attachment can be, for example, depending on the material used for the electrodes, of the chemical formula, $X_3$—Si—YR", $X_2$—Si—(N)YR", and X—Si—(N$_2$)YR" where X is a leaving group, such as for example, —Cl, —OCH$_3$, or —OCH$_2$CH$_3$, R" is a reactive coupling group, such as for example, —NH$_2$, —COOH, —COH, —CHCH$_2$, or —SH, and N is a nonreactive group, such as, for example, an alkyl group. The organic group presented by the surface-attached silane molecule for coupling can be, for example, a carboxylic group, an aldehyde, an ester, an alkene, an alkyne, a thiol, an isocyanate, an isothiocyanate, a substituted amine, an epoxide, a small molecule such as biotin, or an alcohol. In general, Y is a nonreactive group, such as, a hydrocarbon having from 1 to 16 carbon atoms. Examples of —YR" include, —(CH$_2$)$_3$NH$_2$, —(CH$_2$)$_2$COOH, and —(CH$_2$)$_2$SH. Some exemplary silanes include, 3-aminopropyltriethoxysilane (APTS), mercaptosilane, and glycidoxytrimethoxysilane (having an epoxide reactive coupling group). Other functional groups and silanes are also possible. A surface to be silanated can be reacted with a silane molecule, for example, in solution or as a silane gas.

Dielectric materials also include, for example, silicon dioxide, silicon nitride, siliconoxynitride, carbon doped oxide (CDO), silicon carbide, organic polymers such as perfluorocyclobutane or polytetrafluoroethylene, fluorosilicate glass (FSG), and/or organosilicates such as silsesquioxane, siloxane, or organosilicate glass. Dielectric materials can also include polymers, such as, for example, polyimide.

Because the background current with the conducting diamond electrode was found to be small, it is possible to record measurements on small numbers of molecules using only one of the two working electrodes. Measurements can be recorded on as few as one molecule. In alternate embodiments, measurements recorded at both of the electrodes are used to generate the signal. A system for measuring and recording electrode potentials and current flow in nanogap transducers includes, for example, a bipotentiostat. Using a bipotentiostat, the potential of both electrodes versus the solution potential is controlled and the current flowing through the electrodes is measured. Some or all of the parts of a system for driving electrodes and measuring and recording current flow can be located in an integrated circuit (IC) chip that is electrically coupled to an array of individually addressable nanogap transducers housed on the IC chip. In embodiments of the invention, a computer system associated with the array of individually addressable nanogap transducers comprises software for measuring and recording electrode potential and current values using measurements from only one electrode where the electrode is comprised of conducting diamond. In alternate embodiments the computer system includes software for measuring and recording electrode potentials from two electrodes and/or both two electrodes and one electrode. Techniques such as electrochemical correlation spectroscopy can be used to produce a signal from measurements from two oppositely biased electrodes in a nanogap device.

In general, electronic sensors employing electrodes, such as nanogap transducers, are capable of measuring the impedance, the resistance, the capacitance, and/or the redox potential of the materials that are located on or near the electrode surface. The substrate on which the nanogap transducers reside may also include detection and/or drive circuits, logic for switching, latches, memory, and/or input/output devices. Optionally some or all of the electronics for sensing and driving electrodes and recording data are integrated circuits that are part of the substrate that houses an array of nanogap transducers. Electronics providing input and output control are optionally housed in the substrate, such as in an integrated circuit chip, or are provided through circuitry that is external the substrate. An array of nanogap transducers is optionally equipped with, circuitry for individually addressing the electrodes, driving the electrodes at selected voltages, memory for storing voltage current information to be supplied to the electrodes, memory and microprocessors for measuring electrode characteristics, differential amplifiers, current-sensing circuits (including variants of circuits used in CMOS image sensors), and/or field effect transistors (direct and floating gate). Alternatively, one or more of these functions can be performed by external instruments and/or attached computer system(s).

In a redox cycling measurement, oppositely biased electrodes are used to repeatedly flip the charge state of redox active molecules in solution allowing each redox active molecule to participate in multiple redox reactions and thereby contribute multiple electrons to a measured current value. In redox cycling measurements, the height of the gap between the electrodes is on the nanometer scale. Redox active molecules in the cavity between the two electrodes shuttle multiple electrons between the electrodes, leading to amplification of the measured electrochemical current. Signals from the redox active species can potentially be amplified greater than 100 times, depending on factors such as the stability of the redox species and the ability of the redox species to diffuse out of the sensing region.

In embodiments of the invention, electrodes in the nanogap transducer are independently biased at the oxidation and reduction potential of the redox species to be detected. Redox species act as charge shuttles and the diffusion of the molecules from one electrode to the other results in the reduction and oxidation of the redox molecule and a net charge transfer. The magnitude of current through either electrode is proportional to the analyte (redox species) concentration in the cavity. The gaps between the electrodes are optionally sealed with beads to prevent the diffusion of the redox active species out of the cavity, thereby increasing the effective concentration of the redox species. Sealing of the cavity can prevent the escape of redox species from the cavity during sensor measurements.

In general, a redox active species is a molecule that is capable of reversibly cycling through states of oxidation and/or reduction a plurality of times.

In embodiments of the invention, nanogap transducers can be arrays of individually-addressable nanogap transducers. Arrays are built having a variety of dimensions and numbers of nanogap transducer. The selection of number layout of nanogap transducers is informed by factors such as, for example, the types and numbers of analytes to be detected, the size of the sensing regions, and costs involved in manufacturing the arrays. For example, arrays of nanogap transducers are 10×10, 100×100, 1,000×1,000, $10^5 \times 10^5$, and $10^6 \times 10^6$. Very high density, high density, moderate density, low density, or very low density arrays can be made. Some ranges for very high-density arrays are from about 100,000,000 to about 1,000,000,000 sensors per array. High-density arrays range from about 1,000,000 to about 100,000,000 sensors. Moderate density arrays range from about 10,000 to about 100,000 sensors. Low-density arrays are generally less than 10,000 cavities. Very low-density arrays are less than 1,000 sensors.

An array of individually addressable nanogap transducers can be housed on and electrically coupled to an IC chip. The IC chip is typically built on a semiconductor substrate, such as, a semiconductor wafer that is diced apart to yield individual IC chips. The base substrate on which an IC chip is built is typically a silicon wafer, although embodiments of the invention are not dependent on the type of substrate used. The substrate could also be comprised of germanium, indium antimonide, lead telluride, indium arsenide, indium phosphide, gallium arsenide, gallium antimonide, and/or other group III-V materials either alone or in combination with silicon or silicon dioxide or other insulating materials. Layers and layers comprising devices can also be described as the substrate or part of the substrate on which embodiments of the invention are housed or fabricated.

The nanogap transducer arrays allow, for example, a large number of immobilized DNA molecules to be sequenced simultaneously, although other uses are also possible. The immobilized DNA molecules can either be a sample to be sequenced or capture DNA probes of known sequence can be first immobilized and then the sample to be sequenced can be hybridized to the immobilized probes. The capture probes have a sequence designed to hybridize to sections of the sample DNA. In embodiments of the invention, DNA fragments (or capture probes) to be immobilized are diluted so that statistically each sensor has one DNA molecule immobilized. Sequence information is assembled from the nanogap transducers having a single DNA molecule immobilized. Information from nanogap transducers showing ambiguous results can be disregarded.

Figure 8:
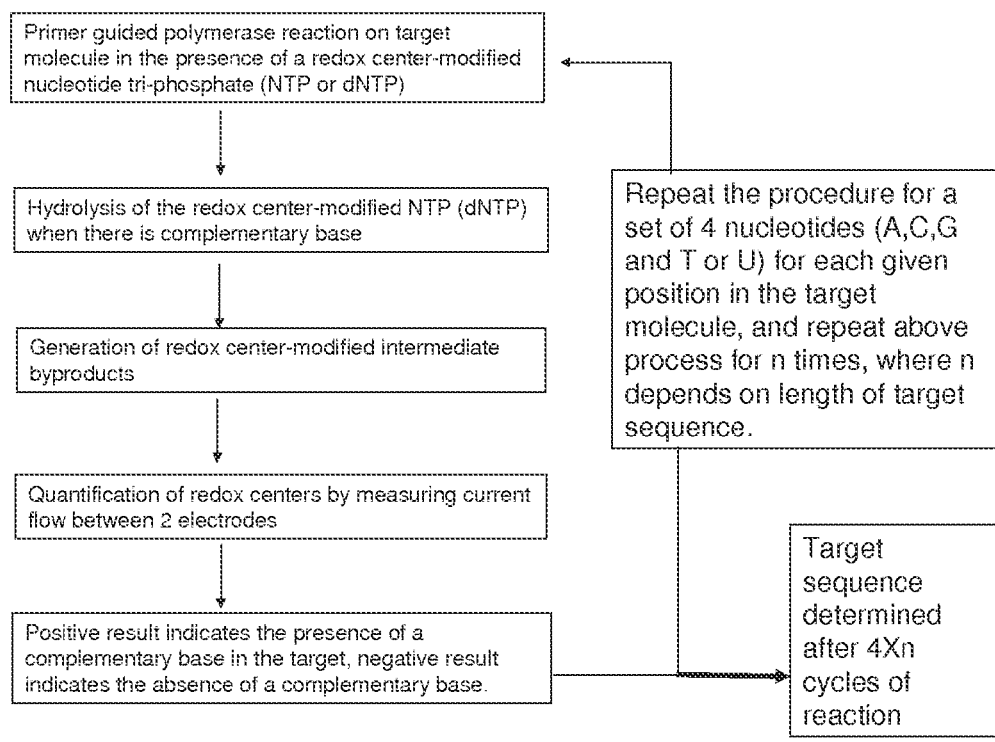
FIG. 8 provides a flow diagram of a method for determining the sequence of a nucleic acid molecule.

Methods are provided for sequencing nucleic acids in which amplification of the nucleic acid sample (i.e., increasing the number of copies of the nucleic acid molecules in the sample) optionally does not have to occur. FIG. 8 provides a flow diagram describing a method that is useful for sequencing a nucleic acid molecule, SNP (single nucleotide polymorphism) detection, and gene expression detection. In FIG. 8, a nucleic acid molecule is attached to a surface inside an electronic sensor. A solution is provided to the sensor cavity containing a primer complementary to a section of the nucleic acid target. The primer DNA molecule hybridizes to a section of the DNA molecule attached inside the cavity and primes the attached DNA molecule for synthesis of a complementary strand of DNA. If the sequence of DNA inside the cavity is unknown, the primer might be one of many having random sequences provided to the DNA strand inside the sensor. The primer can be terminated with a nuclease-resistant nucleotide. After the primer is allowed to hybridize to the DNA molecule inside the cavity, a solution containing a DNA polymerase enzyme and a redox-center modified nucleotide triphosphate (NTP or dNTP) is added. The dNTP contains either a reodox modified deoxyadenosine triphosphate (dATP), deoxycytidine triphosphate (dCTP), deoxyguanosine triphosphate (dGTP), deoxythymidine triphosphate (dTTP), or uridine triphosphate (UTP). For example, if a redox-modified dATP has been provided and thymidine is the next complementary nucleic acid in the sequence, then the redox-modified dATP is incorporated into the growing DNA strand. Where there is a cytosine on the strand to be sequenced, a guanine will be incorporated, where there is a thymidine, an adenosine will be incorporated, and vice versa. If dATP is not the next complementary nucleic acid, then no chemistry occurs inside the sensor cavity. Products of the reaction are then detected. If no reaction has occurred, then the redox-center modified reaction products are not detected. Thus, a positive result (the detection of redox-center modified reaction products) indicates that dATP (in this example) is the next complementary nucleic acid in the growing chain. If a negative result is found, this method is then repeated for the three remaining redox-center modified nucleotides until a positive result is achieved to determine the identity of the complementary base. After the identity of a nucleotide has been determined, the growing strand of complementary DNA can be terminated with a nuclease resistant nucleotide.

Figure 9:
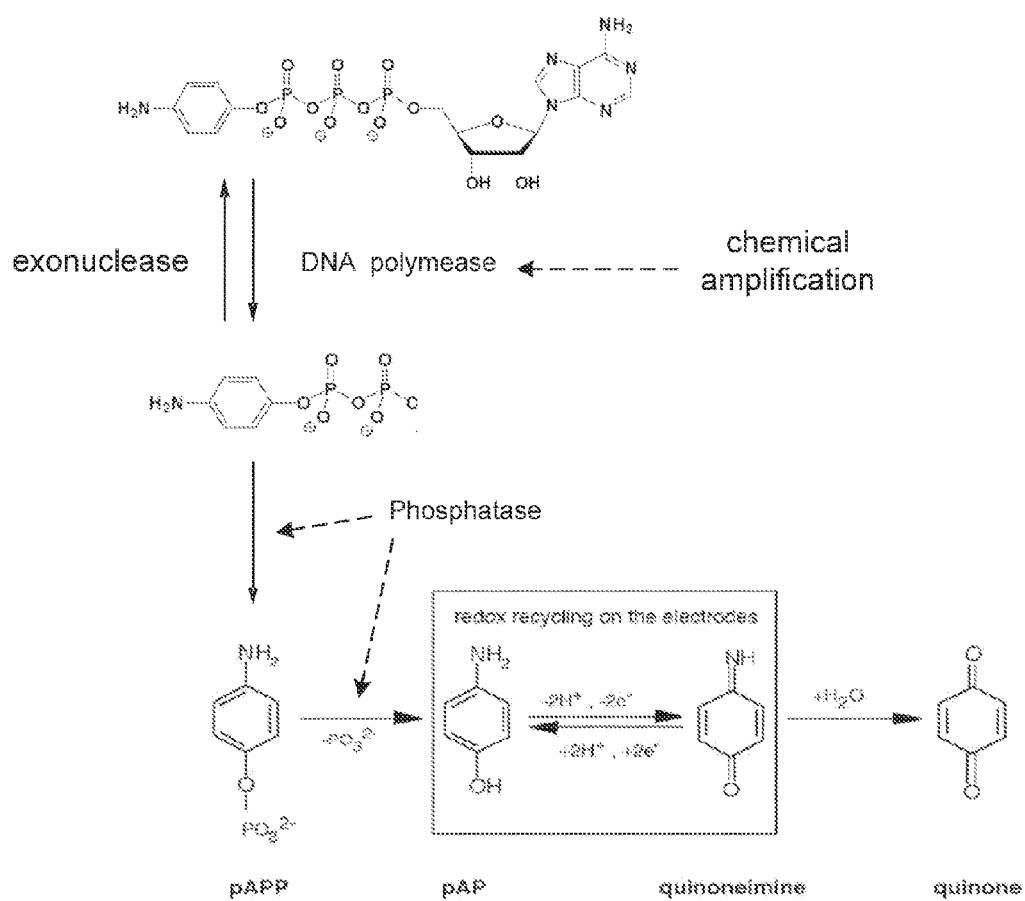
FIG. 9 provides a reaction scheme showing a method for sequencing a nucleic acid molecule through the detection of an oxidation-reduction reaction of a redox active species.

FIG. 9 illustrates a method for sequencing a DNA molecule through chemically amplifying the redox signal obtained when a nucleotide base is complementary to the base provided by the template strand being sequenced. The method of FIG. 9 provides for chemical amplification of the signal when a complementary base in incorporated into a growing complementary strand. The primed growing DNA molecule is terminated with a nuclease resistant base through the action of a polymerase enzyme. In this example, the redox labeled NTP is γ-aminophenyl-adenine-triphosphate (dATP). The incorporation of a complementary redox labeled nucleotide into the growing strand releases the redox labeled pyrophosphate (PPi) group into solution. The action of a phosphatase enzyme removes the pyrophosphate from the redox molecule. Useful phosphatase enzymes include, for example, alkaline phosphatase, acid phosphatase, protein phosphatase, polyphosphate phosphatase, sugar-phosphatase, and pyrophosphatase. In this example, the redox active species is the p-aminophenol (pAP) and quinoneimine pair. The number of p-aminophenol molecules released into solution is amplified through the cycling of the redox labeled NTP incorporation and excision reactions. Specifically, a complementary redox labeled nucleotide is incorporated, an exonuclease enzyme removes the incorporated complementary nucleotide, and then DNA polymerase incorporates a second redox labeled complementary nucleotide and a second redox labeled pyrophosphate group is released into solution. Through these repeated cycles of incorporation and removal, the concentration of the redox active species builds up in solution. In this way, the signal resulting from the incorporation of a complementary base into the growing complementary strand is amplified. The removal of the phosphate groups activates the redox active species. The presence of the redox active species tree of phosphate groups is detected electrochemically. The redox active species can be recycled between two electrodes of a nanogap transducer to amplify the signal further via a redox cycling reaction. As described more fully herein, the signal amplification technique of cycling redox active species between electrodes is referred to as redox cycling. By moving between electrodes of a nanogap transducer, each redox active species contributes multiple electrons to the measured current, thereby amplifying the measured current. If the nucleotide supplied to the reaction is not complementary to the growing DNA strand, then the free redox active species is not detected. Once a nucleotide incorporation has been detected, the growing strand is provided with a nuclease-resistant base that is complementary to the next space in the template DNA molecule that is being sequenced.

A redoxigenic nucleotide has a redox active species attached to the γ-phosphate group of the nucleoside. The base for the redoxigenic nucleotide may be an A, G, C, or T. Redox active species include, for example, aminophenyl, hydroxyphenyl, and/or napthyl groups. A redox active species may also be attached to the nucleotide base. The base may be an A, G, C, or T and the redox active species may be, for example a ferrocene, an anthraquinone, or a methylene blue molecule. A third redox active group attachment motif includes one in which the redox active group is attached to the sugar group of the nucleotide base. For the sugar-attached redox-modified nucleotide, the base may be an A, G, C, or T and the redox active species may be, for example a ferrocene, an anthraquinone, or a methylene blue molecule.

Polymerases are available that can incorporate ribonucleotides or modified nucleotides into DNA, such as for example, the commercially available Therminator DNA polymerase (available from New England Biolabs, Inc., Beverly, Mass.) or genetically engineered DNA polymerase. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997), Nuclease-resistant nucleotides can be ribonucleotides or other modified nucleotides. Exemplary nuclease resistant bases that can be incorporated into growing DNA strands but that are resistant to digestion by exonucleases (such as the 3' to 5' exonuclease active DNA polymerases or exonuclease I and III) include alpha phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases, but the ribonucleotide bases are resistant to digestion by exonucleases, such as exonucleases I or exonuclease III (available from New England Biolabs). Exemplary nucleases that cannot digest these resistant bases include exonuclease I, nuclease III, and 3' to 5' exonuclease active DNA polymerases.

In embodiments of the invention, a single nucleic acid molecule to be sequenced is attached to a surface inside a nanogap transducer. The nucleic acid is primed with a complementary strand that is terminated with a nuclease resistant nucleotide. A complementary redox-modified dNTP molecule is incorporated into the growing strand through the action of a DNA polymerase enzyme present in the solution in the nanogap transducer cavity. The electrodes of the nanogap transducer are oppositely biased at the redox potential of the redox species, and when the redox species is present, a current flow is detected at the electrode surfaces. The excess redox-modified dNTP from the polymerase reaction is washed away from the reaction site. Any incorporated dNMP is then excised from the growing complementary DNA strand through the action of a nuclease enzyme present in the solution in the electrode cavity. This method is then optionally repeated for the three other nucleotides. Once the next complementary nucleotide has been determined, the growing complementary nucleic acid strand can be terminated with a complementary nuclease resistant base and the next complementary base can be determined.

In alternate embodiments, more than one copy of the nucleic acid molecule to be sequenced is attached in the electrode cavity. The attachment of a plurality of copies of the nucleic acid to be sequenced amplifies the signal detected when a complementary nucleotide triphosphate is provided to the cavity. The detected signal can then optionally be amplified further through redox cycling techniques.

Nucleic acid sequencing can be performed in a massively parallel manner using arrays of individually addressable nanogap transducers. A sample comprising nucleic acid molecules is presented to the array in a manner that results in statistically one nucleic acid molecule per reaction cavity. Electronics coupled to the reaction cavities detect the incorporation of nucleic acids in the cavities. Data from cavities that is inconsistent can be discarded. Sequence information for each nucleic acid in a cavity is built through multiple reaction cycles.

One or more surfaces of the nanogap transducer can be optionally functionalized with, for example, one of or combination of amine, aldehye, epxoy, thiol, groups, and molecules to be attached are functionalized with amine (for surface bearing carboxy, epoxy, and/or aldehyde functional groups) and carboxyl (for surface bearing amine groups), thiol (for surface of gold) to facilitate molecular attachment. Various conjugation chemistries are available to join the functional groups (for example, EDC for amine-carboxyl). The concentration of molecules on the substrate surface is controlled, for example, in several ways: by limiting the density of surface functional groups or by limiting the quantity of molecules to be attached. DNA is immobilized on a surface, for example, by using acrydite-modified DNA fragments that are attached to a surface modified with thiol groups. Amine-modified DNA fragments can be attached to epoxy or aldehyde modified surfaces.

A sensor system including one or more arrays of nanogap transducers (such as an array of nanogap transducers on a IC device surface), electronics for driving the transducers and recording measurements, and a computer for recording an analyzing data, can also include fluid delivery systems that are capable of delivering fluids to the nanogap transducers. The fluidic system can comprise reservoirs for reagents, pumps and mixing chambers, washing solutions, waste chambers, and fluid delivery systems that deliver fluids to the surface of an array of nanogap transducers.

In general, the types of nucleic acids that can be sequenced include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine, or uracil linked to ribose. However, a polynucleotide or oligonucleotide also can contain nucleotide analogs, including non-naturally occurring synthetic nucleotides or modified naturally occurring nucleotides.

Data from the sensors can be analyzed as follows. If a nanogap transducer has more than one DNA molecule attached within its cavity, there will be more than one possible reading from at least one of the sequenced positions. Therefore, only data from those nanogap transducers having one molecule attached in the nanogap transducer cavity (an effective sensor) are used in the sequence analysis. Sequences of effective sensors are aligned by computer program. The sequence information can be used as de novo sequencing information or reference sequencing information. Further analysis is performed depending on the quality of the data and purpose of the sequencing task.

Additionally, nanogap transducers according to embodiments of the invention are capable of performing a variety of biologically important detections which are not limited to those described herein. For example, nanogap transducers are capable of detecting mutations in DNA and identifying pathogens through DNA sequencing reactions. Additionally, electronic sensors are used to diagnose diseases through assaying metabolic enzyme activities. Pyrophosphate is a byproduct of many enzymatic reactions that are part of metabolic and signal transduction pathways. Nanogap transducers according to embodiments can be provided with recognition and binding sites for a target analyte. The nanogap transducer is created having the recognition and binding site of interest and a test is performed on a sample solution by exposing the sample solution to the analyte binding region of the biosensor device to allow binding of any specifically recognized biomolecules of interest. The nanogap transducer(s) can be integrated into micro- or nanofluidic systems that provides filtering and sample purification functions. Thus, an enzyme to be tested for functionality is bound in the electronic biosensor and a reaction solution is provided in which a reaction product is PPi labeled with a redox center. For example, a biosensor device probes the functionality of adenylating enzymes that convert fatty acids to acyl adenylate and produce PPi by binding the adenylating enzyme of interest in the biosensor device and providing fatty acid substrates as well as ATP in a reaction solution. Additional examples include catechols. In further examples, living microbes are specifically bound to biosensors. Microbes are optionally bound in the sensing device through an antibody that specifically recognizes a surface antigen on the microbe. Antibody sandwich assays are performed. In the antibody sandwich assay, an electronic sensor is provided having an antibody specific for the molecule to be detected, the sensor is exposed to the molecule to be detected, and a second antibody specific for a different epitope of the molecule to be detected is bound to the molecule to be detected. The second antibody has an attached molecule capable of converting redox labeled ATP to redox labeled PPi. The redox labeled PPi is detected through redox cycling. Redox labels include, for example, ferrocene, anthraquinone, and methylene blue molecules, and aminophenyl, hydroxyphenyl, and/or napthyl groups.

A computer or computer system comprises a processing system, including one or more processors that are communicatively coupled to one or more volatile or non-volatile data storage devices, such as random access memory (RAM), read-only memory (ROM), mass storage devices such as serial advanced technology attachment (SATA) or small computer system interface (SCSI) hard drives, and/or devices capable of accessing media, such as floppy disks, optical storage, tapes, flash memory, memory sticks, CD-ROMs and/or digital video disks (DVDs). The term ROM refers to non-volatile memory devices such as erasable programmable ROM (EPROM), electrically erasable programmable ROM (EEPROM), flash ROM, and/or flash memory. The processor can also be communicatively coupled to additional components, such as graphics controllers, memory interface hubs, SCSI (small computer system interface) controllers, network controllers, network interfaces, and universal serial bus (USB) controllers. Some or all of the communications between elements of the computer system, additional processors, and/or external computers and computer networks can also occur using various wired and/or wireless short range protocols including, USB, WLAN (wireless local area network), radio frequency (RF), satellite, microwave, Institute of Electrical and Electronics Engineers (IEEE) 802.11, Bluetooth, optical, fiber optical, infrared, cables, and lasers. Typically a computer system is also coupled to other input/output devices, such as, for example, display screens, keyboards, trackpads, mice.

Persons skilled in the relevant art appreciate that modifications and variations are possible throughout the disclosure as are substitutions for various components shown and described. Reference throughout this specification to "one embodiment" or "an embodiment" means that a particular feature, structure, material, or characteristic described in connection with the embodiment is included in at least one embodiment of the invention, but does not necessarily denote that they are present in every embodiment. Furthermore, the particular features, structures, materials, or characteristics disclosed in the embodiments may be combined in any suitable manner in one or more embodiments. Various additional layers and/or structures may be included and/or described features may be omitted in other embodiments.

We claim:

1. A device comprising,
a substrate having a surface, and
a transducer disposed on the substrate surface, wherein the transducer comprises:
a first electrode and a second electrode wherein the first and the second electrodes are each coupled to conducting lines through which voltage can be applied to the first and second electrodes independently and a current measured from each of the first and second electrodes independently, and wherein the first electrode has a face and the second electrode has a face and the face of the first electrode is separated from the face of the second electrode by a distance that is less than 500 nm,
a cavity capable of containing a fluid between the face of the first electrode and the face of the second electrode,
an access hole through the second electrode that is capable of allowing a fluid to enter and leave the cavity,
a layer of preferentially functionalizable dielectric material disposed on the second electrode wherein the preferentially functionalizable dielectric layer has an exposed surface within the access hole, and
a layer of dielectric material that is not preferentially functionalizable disposed on the layer of preferentially functionalizable dielectric material.

2. The device of claim 1 wherein the face of the first electrode is separated from the face of the second electrode by a distance that is between 10 and 200 nm.

3. The device of claim 1 wherein the exposed surface of the preferentially functionalizable dielectric layer comprises a surface-attached silane or sulfur-containing molecule.

4. The device of claim 1 wherein the first or the second electrode is comprised of conducting diamond.

5. The device of claim 1 wherein both the first and second electrodes are comprised of conducting diamond.

6. The device of claim 1 wherein the first electrode is comprised of nanocrystalline conducting diamond.

7. The device of claim 1 wherein the first and the second electrodes are comprised of a material selected from the group consisting of conducting diamond, gold, and platinum.

8. The device of claim 1 wherein the substrate is an integrated circuit chip and the first electrode and the second electrode are independently electrically coupled to electronics within the integrated circuit chip through the conducting lines.

9. A device comprising,
a substrate having a surface, and
a transducer disposed on the substrate surface, wherein the transducer comprises:
a first electrode and a second electrode wherein the first and the second electrodes are each coupled to conducting lines through which voltage can be applied to the first and second electrodes independently and a current measured from each of the first and second electrodes independently, and wherein the first electrode has a face and the second electrode has a face and the face of the first electrode is separated from the face of the second electrode by a distance that is less than 500 nm, a cavity capable of containing a fluid between the face of the first electrode and the face of the second electrode, an access hole through the second electrode that is capable of allowing a fluid to enter and leave the cavity, a preferentially functionalizable dielectric region disposed on a region of the face of the first electrode wherein the preferentially functionalizable dielectric region comprises an exposed surface, and a layer of dielectric material that is not preferentially functionalizable coupled to the preferentially functionalizable dielectric region.

10. The device of claim 9 wherein the face of the first electrode is separated from the face of the second electrode by a distance that is between 10 and 200 nm.

11. The device of claim 9 wherein the preferentially functionalizable dielectric region has an exposed surface area of 40 nm.sup.2 to 500,000 nm.sup.2.

12. The device of claim 9 wherein the exposed surface of the preferentially functionalizable dielectric region comprises a surface-attached silane or sulfur-containing molecule.

13. The device of claim 9 wherein the first or the second electrode is comprised of conducting diamond.

14. The device of claim 9 wherein the first electrode is comprised of nanocryastalline conducting diamond.

15. The device of claim 9 wherein both the first and second electrodes are comprised of conducting diamond.

16. The device of claim 9 wherein the first and the second electrodes are comprised of a material selected from the group consisting of conducting diamond, gold, and platinum.

17. A device comprising,
a substrate having a surface, and
a transducer disposed on the substrate surface, wherein the transducer comprises:
a first electrode and a second electrode wherein the first and the second electrodes are each coupled to conducting lines through which voltage can be applied to the first and second electrodes independently and a current measured from each of the first and second electrodes independently, and wherein the first electrode has a face and the second electrode has a face and the face of the first electrode is separated from the face of the second electrode by a distance that is less than 500 nm,
a cavity capable of containing a fluid between the face of the first electrode and the face of the second electrode,
an access hole through the second electrode that is capable of allowing a fluid to enter and leave the cavity,
a preferentially functionalizable region in the first electrode wherein the first electrode is disposed on the substrate surface, wherein the first electrode comprises a hole, wherein the preferentially functionalizable region comprises a region of the substrate surface that is exposed through the hole in the first electrode, and
a layer of dielectric material that is not preferentially functionalizable coupled to the layer of preferentially functionalizable dielectric region.

18. The device of claim 17 wherein the face of the first electrode is separated from the face of the second electrode by a distance that is between 10 and 200 nm.

19. The device of claim 17 wherein the preferentially functionalizable region has an exposed surface area of 40 nm.sup.2 to 500,000 nm.sup.2.

20. The device of claim 17 wherein the preferentially functionalizable region comprises a surface-attached silane or sulfur-containing molecule.

21. The device of claim 17 wherein the first or the second electrode is comprised of conducting diamond.

22. The device of claim 17 wherein the first electrode is comprised of nanocryastalline conducting diamond.

23. The device of claim 17 wherein both the first and second electrodes are comprised of conducting diamond.

24. The device of claim 17 wherein the first and the second electrodes are comprised of a material selected from the group consisting of conducting diamond, gold, and platinum.

25. A system comprising,
a computer operably coupled to a integrated circuit chip wherein the integrated circuit chip comprises an array of transducers disposed on a surface of the integrated circuit chip,
a fluidic system capable of supplying fluids to the surface of the integrated circuit chip comprising the array of transducers,
wherein transducers that make up the array are electrically coupled to and individually addressable through electronics in the integrated circuit chip, and wherein a transducer comprises:
a first electrode and a second electrode wherein the first and the second electrodes are each coupled to conducting lines through which voltage can be applied to the first and second electrodes independently and a current measured from each of the first and second-electrodes independently, and wherein the first electrode has a face and the second electrode has a face and the face of the first electrode is separated from the face of the second electrode by a distance that is less than 500 nm,
a cavity capable of containing a fluid between the face of the first electrode and the face of the second electrode,
an access hole through the second electrode that is capable of allowing a fluid to enter and leave the cavity,
a preferentially functionalizable dielectric region disposed on a region of the face of the first electrode wherein the preferentially functionalizable dielectric region comprises an exposed surface, and
a layer of dielectric material that is not preferentially functionalizable coupled to the preferentially functionalizable dielectric regions.

26. The device of claim 25 the face of the first electrode is separated from the face of the second electrode by a distance that is between 10 and 200 nm.

27. The device of claim 25 wherein the preferentially functionalizable dielectric region has an exposed surface area of 40 nm.sup.2 to 500,000 nm.sup.2.

28. The device of claim 25 wherein the exposed surface of the preferentially functionalizable dielectric region comprises a surface-attached silane or sulfur-containing molecule.

29. The device of claim 25 wherein the first or the second electrode is comprised of conducting diamond.

30. The device of claim 25 wherein the first electrode is comprised of nanocryastalline conducting diamond.

31. The device of claim 25 wherein both the first and second electrodes are comprised of conducting diamond.

32. The device of claim 25 wherein the first and the second electrodes are comprised of a material selected from the group consisting of conducting diamond, gold, and platinum.

33. The device of claim 25 wherein the array comprises at least 1000 transducers.

34. The device of claim 25 wherein the computer is configured to perform data analysis using current measurements from one of the first or the second electrode wherein the one of the first or second electrode from which the current is measured is comprised of conducting diamond.

* * * * *